United States Patent
Soane et al.

(10) Patent No.: US 10,016,513 B2
(45) Date of Patent: *Jul. 10, 2018

(54) STABILIZING EXCIPIENTS FOR THERAPEUTIC PROTEIN FORMULATIONS

(71) Applicant: REFORM BIOLOGICS, LLC, Cambridge, MA (US)

(72) Inventors: David S. Soane, Palm Beach, FL (US); Robert P. Mahoney, Newbury, MA (US); Philip Wuthrich, Belmont, MA (US); Daniel G. Greene, Belmont, MA (US)

(73) Assignee: Reform Biologics, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,168

(22) Filed: Aug. 14, 2017

(65) Prior Publication Data

US 2018/0015169 A1 Jan. 18, 2018

Related U.S. Application Data

(63) Continuation of application No. 15/647,669, filed on Jul. 12, 2017.

(60) Provisional application No. 62/361,793, filed on Jul. 13, 2016.

(51) Int. Cl.
*A61K 38/00* (2006.01)
*A61K 47/54* (2017.01)
*C08G 73/02* (2006.01)

(52) U.S. Cl.
CPC ............ *A61K 47/543* (2017.08); *A61K 38/00* (2013.01); *C08G 73/0233* (2013.01)

(58) Field of Classification Search
CPC ... A61K 47/543; A61K 38/00; C08G 73/0233
USPC ........................................................ 514/788
See application file for complete search history.

(56) References Cited

U.S. PATENT DOCUMENTS

| | | |
|---|---|---|
| 4,013,416 A | 3/1977 | Rittersdorf et al. |
| 6,039,977 A | 3/2000 | Venkatraman et al. |
| 8,633,034 B2 | 1/2014 | Trotter et al. |
| 8,802,603 B2 | 8/2014 | D'Souza et al. |
| 2008/0287417 A1 | 11/2008 | Ebner et al. |
| 2011/0046052 A1 | 2/2011 | Yang |
| 2014/0057861 A1 | 2/2014 | Yan et al. |
| 2014/0065159 A1 | 3/2014 | Ma et al. |
| 2016/0068609 A1 | 3/2016 | Goletz et al. |
| 2016/0074515 A1 | 3/2016 | Soane et al. |

OTHER PUBLICATIONS

Thurow et al. Diabetologia, 1984, 27, 212-218.*
Krayukhina, E., et al., "Effects of Syringe Material and Silicone Oil Lubrication on the Stability of Pharmaceutical Proteins," Journal of Pharmaceutical Sciences, 104: 527-535 (2015).

* cited by examiner

*Primary Examiner* — Yevgeny Valenrod
(74) *Attorney, Agent, or Firm* — Elmore Patent Law Group, P.C.; Mahreen Hoda; Carolyn Elmore

(57) ABSTRACT

The invention encompasses therapeutic formulations comprising a protein active ingredient and a stabilizing excipient, methods of improving stability in a therapeutic formulation comprising a protein active ingredient by adding a stability-improving amount of a stabilizing excipient to the therapeutic formulation, and methods of reducing adverse infusion-related effects in a patient, comprising administering to a patient in need thereof a therapeutic formulation comprising a protein active ingredient and a stabilizing excipient.

26 Claims, No Drawings

STABILIZING EXCIPIENTS FOR THERAPEUTIC PROTEIN FORMULATIONS

RELATED APPLICATIONS

This application is a continuation of U.S. application Ser. No. 15/647,669, filed on Jul. 12, 2017, claims the benefit of U.S. Provisional Application Ser. No. 62/361,793, filed Jul. 13, 2016. The entire contents of the above applications are incorporated by reference herein.

FIELD OF THE APPLICATION

This application relates to formulations for stabilizing therapeutic proteins.

BACKGROUND

Aqueous formulations of therapeutic proteins (e.g., antibodies) are susceptible to degradation through a number of different mechanisms and as a result of several types of stress conditions. In general, degradation of a therapeutic protein formulation occurs when the protein structure is altered slightly from its fully folded conformation (partial unfolding) exposing hydrophobic residues that interact with an adjacent protein molecule in solution forming an irreversible association. Certain stress conditions such as agitation, freeze/thaw and increased temperature can induce greater protein unfolding leading to accelerated aggregation of the protein and degradation of the protein formulation. Degradation of the protein formulation can be manifested by protein denaturation, the formation of visible particles, the formation of aggregates, the formation of subvisible particles, opalescence of the formulation, loss of biological activity, loss of percent monomer, loss of yield during production and purification, and the like. Exposure of the protein formulation to a liquid/air or liquid/solid interface, such as in agitation or freeze/thaw conditions, allows for a portion of the protein to unfold because of the lack of water at the interface to stabilize the folded structure through hydrogen bonding and hydrophobic effects. Other mechanisms leading to protein degradation include oxidation, hydrolysis, proteolysis, photodegradation, and microbial degradation. It would be desirable to provide a therapeutic protein formulation with improved stability to make the therapeutic proteins more resistant to the stress conditions encountered during their distribution and storage. For example, formulations of therapeutic proteins can encounter stress conditions like freeze/thaw cycles, agitation, long term storage, pumping, filtration, or unrefrigerated storage, where improvements to stability would be advantageous.

In conventional protein formulations, a small amount of a nonionic surfactant, typically Polysorbate 80 or Polysorbate 20, is added to compete with the protein for interfacial surfaces to reduce protein degradation that occurs with its exposure to such surfaces. However, polysorbates themselves can degrade, either through hydrolysis or oxidation, and the resulting degradation products promote aggregation and/or reduce solubility of the protein and destabilize protein formulations. Polysorbates also pose a problem during the manufacturing process of protein therapeutics because of their tendency to form micelles. The formation of micelles can prevent some of the polysorbate from passing through filters such as during an ultrafiltration/diafiltration unit operation, causing a significantly larger polysorbate concentration in the drug substance than intended. For these reasons it is desirable to have a protein formulation that minimizes or is substantially free from conventional surfactants such as Polysorbate 80 and Polysorbate 20.

SUMMARY

Disclosed herein, in embodiments, are therapeutic formulations comprising a protein active ingredient and a stabilizing excipient. In embodiments, the formulation contains less than about 1 mg/mL of the protein active ingredient, or between about 1 µg/mL and about 1 mg/mL of protein active ingredient, or at least about 1 mg/mL of protein active ingredient, or at least about 5 mg/mL of protein active ingredient, or at least 100 mg/mL of protein active ingredient, or at least about 200 mg/mL of protein active ingredient, or at least about 300 mg/mL of protein active ingredient. In embodiments, the protein active ingredient is selected from the group consisting of an antibody, an antibody-drug conjugate, an enzyme, a cytokine, a neurotoxin, a fusion protein, an immunogenic protein, a PEGylated protein, and an antibody fragment. In embodiments, the formulation contains at least about 1 to about 5000 ppm of the stabilizing excipient, or at least about 1 to about 500 ppm of the stabilizing excipient, or at least about 10 to about 100 ppm of the stabilizing excipient. In embodiments, the stabilizing excipient excludes polypropylene block copolymers.

In certain embodiments, the stabilizing excipient is selected from the group consisting of polypropylene glycol, adducts of polypropylene glycol, and random copolymers comprising propylene oxide units. The stabilizing excipient can be a polypropylene glycol homopolymer, and it can have a number-average molecular weight between about 300 and 5000 Daltons, or a number-average molecular weight of about 425 Daltons, of about 1000 Daltons, or of about 2000 Daltons. In embodiments, the polypropylene glycol homopolymer is a linear polymer with at least two hydroxyl groups, which can contain two or three hydroxyl groups. In embodiments, the polypropylene glycol is a branched polymer, and the branched polymer can be formed by addition of propylene glycol units to a branched or multifunctional alcohol or a branched or multifunctional amine. The branched or multifunctional alcohol can be a sugar, glycerol, pentaerythritol, or triethanolamine. In embodiments, the stabilizing excipient is an adduct of polypropylene glycol. The adduct of polypropylene glycol can be a reaction product between propylene oxide and an alcohol or between propylene oxide and an amine. In certain embodiments, the stabilizing excipient is a hydrophobically modified cellulosic polymer. The hydrophobically modified cellulosic polymer can be selected from the group consisting of a methylcellulose, a hydroxypropyl methylcellulose, a hydroxypropyl cellulose, and a hydroxyethyl cellulose. In embodiments, the hydrophobically modified cellulosic polymer is not a sodium carboxymethyl cellulose. In certain embodiments, the stabilizing excipient is a polyvinyl alcohol, which can have a molecular weight between about 500 and about 500,000 Daltons, and/or which can have a hydrolysis percent between about 50% and about 100%. In certain embodiments, the stabilizing excipient is a polyoxazoline, which can be selected from the group consisting of poly(2-methyl-2-oxazoline), poly(2-ethyl-2-oxazoline) and poly(2-propyl-2-oxazoline). In embodiments, the polyoxazoline is poly(2-ethyl-2-oxazoline). In embodiments, the polyoxazoline has a weight-average molecular weight between about 1000 and about 500,000 Daltons, or a weight-average molecular weight between about 5000 and about 50,000 Daltons. In certain embodiments, the stabilizing excipient is polyvinylpyrrolidone, which can have a molecular weight between about 1000 and about 1,500,000 Daltons, or a molecular weight between about 5000 and about 200,000 Daltons, or a molecular weight between about 10,000 and about 100,000 Daltons.

In embodiments, the formulations disclosed herein can further comprise a second stabilizing excipient. In embodiments, the formulation can exclude conventional surfactants. In other embodiments, the formulation further comprises between about 1 and about 5000 ppm of a conventional surfactant, or it comprises between about 1 and about 100 ppm of the conventional surfactant, or it comprises between about 10 and about 5000 ppm of the conventional surfactant, or it comprises between about 100 and 2000 ppm of the conventional surfactant, or it comprises between about 100 and about 2000 ppm of the conventional surfactant. In other embodiments, the formulation further comprises an additional agent selected from the group consisting of preservatives, sugars, polysaccharides, arginine, proline, hyaluronidase, stabilizers, and buffers.

Also disclosed herein, in embodiments, are methods of improving stability in a therapeutic formulation comprising a protein active ingredient by adding a stability-improving amount of a stabilizing excipient to the therapeutic formulation. In embodiments, the stabilizing excipient reduces degradation of the therapeutic formulation by at least 10%, as compared to a control formulation lacking the stabilizing excipient, or the stabilizing excipient reduces degradation of the therapeutic formulation by at least 30%, as compared to a control formulation lacking the stabilizing excipient, or the stabilizing excipient reduces degradation of the therapeutic formulation by at least 50%, as compared to a control formulation lacking the stabilizing excipient, or the stabilizing excipient reduces degradation of the therapeutic formulation by at least 70%, as compared to a control formulation lacking the stabilizing excipient. Also disclosed herein, in embodiments, are methods of reducing adverse infusion-related effects in a patient, comprising administering to a patient in need thereof a therapeutic formulation comprising a protein active ingredient and a stabilizing excipient, wherein infusing the therapeutic formulation into the patient results in fewer adverse infusion-related effects than infusing a control formulation into the patient, wherein the control formulation lacks the stabilizing excipient. In embodiments, the adverse infusion-related effects are selected from the group consisting of adverse infusion reactions, adverse immunogenic responses, and decrease in half-life of a therapeutic protein in the therapeutic formulation.

DETAILED DESCRIPTION

1. Definitions

For the purpose of this disclosure, the term "protein" refers to a sequence of amino acids (i.e., a polypeptide) typically having a molecular weight between about 1-3000 kiloDaltons (kDa). Polypeptides with molecular weight of about 1 kDa or higher are considered to be proteins for the purposes of the invention. In some embodiments, the molecular weight of the protein is between about 50-200 kDa; in other embodiments, the molecular weight of the protein is between about 20-1000 kDa or between about 20-2000 kDa. As would be understood by skilled artisans, a polypeptide of sufficient chain length can have a tertiary or quaternary structure, while shorter polypeptides can lack a tertiary or quaternary structure. A wide variety of biopolymers are included within the scope of the term "protein." For example, the term "protein" can refer to therapeutic or non-therapeutic proteins, including antibodies, aptamers, fusion proteins, Fc fusion proteins, PEGylated proteins, synthetic polypeptides, protein fragments, lipoproteins, enzymes, immunogenic proteins (e.g., as used in vaccines), structural peptides, peptide drugs, and the like.

Those proteins having therapeutic effects may be termed "therapeutic proteins"; formulations containing therapeutic proteins in therapeutically effective amounts may be termed "therapeutic formulations." The therapeutic protein contained in a therapeutic formulation may also be termed its "protein active ingredient." Typically, a therapeutic formulation comprises a therapeutically effective amount of a protein active ingredient and an excipient, with or without other optional components.

As used herein, the term "therapeutic" includes both treatments of existing disorders and preventions of disorders. A "treatment" includes any measure intended to cure, heal, alleviate, improve, remedy, or otherwise beneficially affect the disorder, including preventing or delaying the onset of symptoms and/or alleviating or ameliorating symptoms of the disorder. The term "treatment" includes a prophylactic or therapeutic vaccine or other preventive intervention.

Those patients in need of a treatment include both those who already have a specific disorder, and those for whom the prevention of a disorder is desirable. A disorder is any condition that alters the homeostatic wellbeing of a mammal, including acute or chronic diseases, or pathological conditions that predispose the mammal to an acute or chronic disease. Non-limiting examples of disorders include cancers, metabolic disorders (e.g., diabetes), allergic disorders (e.g., asthma), dermatological disorders, cardiovascular disorders, respiratory disorders, hematological disorders, musculoskeletal disorders, inflammatory or rheumatological disorders, autoimmune disorders, gastrointestinal disorders, urological disorders, sexual and reproductive disorders, neurological disorders, infectious diseases, and the like.

The term "mammal" for the purposes of treatment can refer to any animal classified as a mammal, including humans, domestic animals, pet animals, farm animals, sporting animals, working animals, and the like. A "treatment" can therefore include both veterinary and human treatments. For convenience, the mammal undergoing such "treatment" can be referred to as a "patient." In certain embodiments, the patient can be of any age, including fetal animals in utero.

In embodiments, a treatment involves providing a therapeutically effective amount of a therapeutic formulation to a mammal in need thereof. A "therapeutically effective amount" is at least the minimum concentration of the therapeutic protein administered to the mammal in need thereof, to effect a treatment of an existing disorder or a prevention of an anticipated disorder (either such treatment or such prevention being a "therapeutic intervention"). Therapeutically effective amounts of various therapeutic proteins that may be included as active ingredients in the therapeutic formulation may be familiar in the art; or, for therapeutic proteins discovered or applied to therapeutic interventions hereinafter, the therapeutically effective amount can be determined by standard techniques carried out by those having ordinary skill in the art, using no more than routine experimentation.

As non-limiting examples, therapeutic proteins can include mammalian proteins such as hormones and prohormones (e.g., insulin and proinsulin, synthetic insulin, insulin analogs, glucagon, calcitonin, thyroid hormones (T3 or T4 or thyroid-stimulating hormone), parathyroid hormone, gastrin, cholecystokinin, leptin, follicle-stimulating hormone, oxytocin, vasopressin, atrial natriuretic peptide, luteinizing hormone, growth hormone, growth hormone releasing factor, somatostatin, and the like); clotting and anti-clotting factors (e.g., tissue factor, von Willebrand's factor, Factor VIIIC, Factor VIII, Factor IX, protein C, plasminogen activators (urokinase, tissue-type plasminogen activators), thrombin); cytokines, chemokines, and inflammatory mediators (e.g., tumor necrosis factor inhibitors); interferons; colony-stimulating factors; interleukins (e.g., IL-1 through IL-10); growth factors (e.g., vascular endothelial growth factors, fibroblast growth factor, platelet-derived growth factor, transforming growth factor, neurotrophic growth factors, insulin-like growth factor, and the like); albumins; collagens and elastins; hematopoietic factors (e.g., erythropoietin, thrombopoietin, and the like); osteoinductive factors (e.g., bone morphogenetic protein); receptors (e.g., integrins, cadherins, and the like); surface membrane proteins; transport proteins; regulatory proteins; antigenic proteins (e.g., a viral component that acts as an antigen, as for example in a vaccine). A therapeutic protein can also be an immunogenic or other protein (including polypeptide) that is used as a vaccine, where a vaccine is a natural or synthetic preparation that induces acquired immunity to a disease. Therapeutic formulations used as vaccines include toxoid vaccines, protein-based or protein subunit-based vaccines, or conjugate vaccines. As an illustrative, non-limiting example, vaccines can contain a surface protein of a virus or a subunit thereof, as in the HPV virus, the Hepatitis B virus, and the influenza virus.

Therapeutic proteins used as vaccines may be derived from natural sources, for example, polypeptides or polypeptide fragments derived from microorganisms such as fungi (e.g., *Aspergillus, Candida* species), bacteria (e.g., *Escherichia* spp., Staphylococci spp., Streptococci spp.), protozoa such as sporozoa (e.g., Plasmodia), rhizopods (e.g., *Entamoeba*) and *flagellates* (*Trypanosoma, Leishmania, Trichomonas, Giardia*, etc.), and viruses, such as (+) RNA viruses, (−) RNA viruses, dsDNA viruses, RNA to DNA viruses, and DNA to RNA viruses. Examples of viruses from which vaccines are derived include without limitation Poxviruses (e.g., vaccinia), Picornaviruses (e.g., polio), Togaviruses (e.g., rubella), Flaviviruses (e.g., HCV); Coronaviruses, Rhabdoviruses (e.g., VSV); Paramyxovimses (e.g., RSV); Orthomyxovimses (e.g., influenza); Bunyaviruses; Arenaviruses, Reoviruses, retroviruses (e.g., HIV, HTLV); and Hepatitis B virus.

The term "therapeutic protein" includes, without limitation, the full complement of proteins that can be used as drugs, for example, fusion proteins such as etanercept, denileukin diftitox, alefacept, abatacept, rinolacept, romiplostim, corifollitropin-alpha, belatacept, aflibercept, ziv-aflibercept, eftrenonacog-alpha, albiglutide, efraloctocog-alpha, dulaglutide, and the like.

The term "therapeutic protein" also includes antibodies. The term "antibody" is used herein in its broadest sense, to include as non-limiting examples monoclonal antibodies (including, for example, full-length antibodies with an immunoglobulin Fc region), single-chain molecules, bi-specific and multi-specific antibodies, diabodies, antibody-drug conjugates, antibody compositions having polyepitopic specificity, and fragments of antibodies (including, for example, Fab, Fv, Fc, and F(ab')2).

Antibodies can also be termed "immunoglobulins." An antibody is understood to be directed against a specific protein or non-protein "antigen," which is a biologically important material; the administration of a therapeutically effective amount of an antibody to a patient can complex with the antigen, thereby altering its biological properties so that the patient experiences a therapeutic effect.

In embodiments, the proteins can be PEGylated, meaning that they comprise polyethylene glycol (PEG) and/or polypropylene glycol (PPG) units. PEGylated proteins, or PEG-protein conjugates, have found utility in therapeutic applications due to their beneficial properties such as improved solubility, improved pharmacokinetics, improved pharmacodynamics, less immunogenicity, lower renal clearance, and improved stability. Non-limiting examples of PEGylated proteins are PEGylated interferons (PEG-IFN), PEGylated anti-VEGF, PEG protein conjugate drugs, Adagen, Pegaspargase, Pegfilgrastim, Pegloticase, Pegvisomant, PEGylated epoetin-$\beta$, and Certolizumab pegol.

PEGylated proteins can be synthesized by a variety of methods such as a reaction of protein with a PEG reagent having one or more reactive functional groups. The reactive functional groups on the PEG reagent can form a linkage with the protein at targeted protein sites such as lysine, histidine, cysteine, and the N-terminus. Typical PEGylation reagents have reactive functional groups such as aldehyde, maleimide, or succinimide groups that have specific reactivity with targeted amino acid residues on proteins. The PEGylation reagents can have a PEG chain length from about 1 to about 1000 PEG and/or PPG repeating units. Other methods of PEGylation include glyco-PEGylation, where the protein is first glycosylated and then the glycosylated residues are PEGylated in a second step. Certain PEGylation processes are assisted by enzymes like sialyltransferase and transglutaminase.

While the PEGylated proteins can offer therapeutic advantages over native, non-PEGylated proteins, these materials can have physical or chemical properties that make them difficult to purify, dissolve, filter, concentrate, and administer. The PEGylation of a protein can lead to a higher solution viscosity compared to the native protein, and this generally requires the formulation of PEGylated protein solutions at lower concentrations.

Those proteins used for non-therapeutic purposes (i.e., purposes not involving treatments), such as household, nutrition, commercial, and industrial applications, may be termed "non-therapeutic proteins." Formulations containing non-therapeutic proteins may be termed "non-therapeutic formulations". The non-therapeutic proteins can be derived from plant sources, animal sources, or produced from cell cultures; they also can be enzymes or structural proteins. The non-therapeutic proteins can be used in in household, nutrition, commercial, and industrial applications such as catalysts, human and animal nutrition, processing aids, cleaners, and waste treatment.

An important category of non-therapeutic biopolymers includes enzymes. Enzymes have a number of non-therapeutic applications, for example, as catalysts, human and animal nutritional ingredients, processing aids, cleaners, and waste treatment agents. Enzyme catalysts are used to accelerate a variety of chemical reactions. Examples of enzyme catalysts for non-therapeutic uses include catalases, oxidoreductases, transferases, hydrolases, lyases, isomerases, and ligases. Human and animal nutritional uses of enzymes include nutraceuticals, nutritive sources of protein, chelation or controlled delivery of micronutrients, digestion aids, and supplements; these can be derived from amylase, protease, trypsin, lactase, and the like. Enzymatic processing aids are used to improve the production of food and beverage products in operations like baking, brewing, fermenting, juice processing, and winemaking. Examples of these food and beverage processing aids include amylases, cellulases, pectinases, glucanases, lipases, and lactases. Enzymes can also be used in the production of biofuels. Ethanol for biofuels, for example, can be aided by the enzymatic degradation of biomass feedstocks such as cellulosic and lignocellulosic materials. The treatment of such feedstock materials with cellulases and ligninases transforms the biomass into a substrate that can be fermented into fuels. In other commercial applications, enzymes are used as detergents, cleaners, and stain lifting aids for laundry, dish washing, surface cleaning, and equipment cleaning applications. Typical enzymes for this purpose include proteases, cellulases, amylases, and lipases. In addition, non-therapeutic enzymes are used in a variety of commercial and industrial processes such as textile softening with cellulases, leather processing, waste treatment, contaminated sediment treatment, water treatment, pulp bleaching, and pulp softening and debonding. Typical enzymes for these purposes are amylases, xylanases, cellulases, and ligninases.

Other examples of non-therapeutic biopolymers include fibrous or structural proteins such as keratins, collagen, gelatin, elastin, fibroin, actin, tubulin, or the hydrolyzed, degraded, or derivatized forms thereof. These materials are used in the preparation and formulation of food ingredients such as gelatin, ice cream, yogurt, and confections; they area also added to foods as thickeners, rheology modifiers, mouthfeel improvers, and as a source of nutritional protein. In the cosmetics and personal care industry, collagen, elastin, keratin, and hydrolyzed keratin are widely used as ingredients in skin care and hair care formulations. Still other examples of non-therapeutic biopolymers are whey proteins such as beta-lactoglobulin, alpha-lactalbumin, and serum albumin. These whey proteins are produced in mass scale as a byproduct from dairy operations and have been used for a variety of non-therapeutic applications.

As used herein, the term "conventional surfactant" refers to an organic surface-active agent capable of lowering the surface tension between two liquids, or lowering the interfacial tension between a liquid and a solid. A conventional surfactant is typically amphiphilic, and can include a hydrophilic "head" and one or two hydrophobic "tails." The charged character of the head group allows categorization of the conventional surfactant: a surfactant with a positively-charged head is termed cationic; a surfactant with a negatively-charged head is termed anionic; a surfactant with no charged groups on its head is termed non-ionic; and a surfactant having a head with two oppositely charged groups is termed zwitterionic. The tail of the conventional surfactant can comprise a branched, linear, or aromatic hydrocarbon chain, or it can comprise a fluorocarbon chain (for fluorosurfactants), or a siloxane chain (for siloxane surfactants). The hydrophilic properties of a conventional surfactant can be increased by including ethoxylated sequences (e.g. polyethylene oxide), while the lipophilic properties of the conventional surfactant can be increased by including polypropylene oxide sequences.

In embodiments, the conventional surfactant can be a polysorbate, i.e., an emulsifier derived from an ethoxylated sorbitan ester of a fatty acid. For example, Polysorbate 20 (polyoxyethylene (20) sorbitan monolaurate) and Polysorbate 80 (polyoxyethylene (20) sorbitan monooleate) are commonly used as conventional surfactants for protein formulations. In other embodiments, the conventional surfactant can be an ethoxylated fatty alcohol, a diblock copolymer of ethylene oxide (EO) and propylene oxide (PO), or a triblock copolymer of EO and PO.

2. General

The present disclosure relates to aqueous formulations of therapeutic proteins with stabilizing excipients. As used herein, the term "stabilizing excipient" refers to an excipient that reduces the degradation of a therapeutic protein in response to a stress condition. A stress condition can be any condition that alters the protein structure, for example, by causing greater protein unfolding, leading to accelerated aggregation and degradation of the protein formulation. Stress conditions can include, without limitation, agitation, filtration, freeze/thaw conditions, lyophilization, exposure to storage temperatures above 5° C., or exposure to a liquid/air or liquid/solid interface. Other mechanisms involved in stress conditions include oxidation, hydrolysis, proteolysis, deamidation, disulfide scrambling, photodegradation, and microbial degradation.

It is well known to those skilled in the art of polymer science and engineering that proteins in solution tend to form entanglements, which can limit the translational mobility of the entangled chains and interfere with the protein's therapeutic or nontherapeutic efficacy. In embodiments, stabilizing excipient compounds as disclosed herein can suppress protein clustering due to specific interactions between the excipient compound and the therapeutic protein in solution.

In embodiments, the approaches disclosed herein can yield a liquid formulation having improved stability when compared to a traditional protein solution. A stable formulation is one in which the protein contained therein substantially retains its physical and chemical stability and its therapeutic or nontherapeutic efficacy upon storage under storage conditions, whether cold storage conditions, room temperature conditions, or elevated temperature storage conditions. Advantageously, a stable formulation can also offer protection against aggregation or precipitation of the proteins dissolved therein. For example, the cold storage conditions can entail storage in a refrigerator or freezer. In some examples, cold storage conditions can entail conventional refrigerator or freezer storage at a temperature of 10° C. or less. In additional examples, the cold storage conditions entail storage at a temperature from about 2° to about 10° C. In other examples, the cold storage conditions entail storage at a temperature of about 4° C. In additional examples, the cold storage conditions entail storage at freezing temperature such as about 0° C. or lower. In another example, cold storage conditions entail storage at a temperature of about −30° C. to about 0° C. The room temperature storage conditions can entail storage at ambient temperatures, for example, from about 10° C. to about 30° C. Elevated temperature stability, for example, at temperatures from about 30° C. to about 50° C., can be used as part of an accelerated aging study to predict the long term storage at typical ambient (10-30° C.) conditions.

In embodiments, advantageous stabilizing excipients can comprise propylene glycol, polypropylene glycol homopolymers, adducts of polypropylene glycol, or random copolymers comprising propylene oxide units. In other embodiments, the stabilizing excipients can comprise a hydrophobically modified cellulose, which can be a methylcellulose, a hydroxypropyl methylcellulose, a hydroxypropyl cellulose, or a hydroxyethyl cellulose, and is not a sodium carboxy methylcellulose. In other embodiments, the stabilizing excipient is polyvinyl alcohol. In other embodiments, the stabilizing excipient is a polyoxazoline, such as poly(2-ethyl-2-oxazoline). In other embodiments, the stabilizing excipient is polyvinyl pyrrolidone.

For example, in embodiments, the stabilizing excipients can comprise a polypropylene glycol (PPG) homopolymer with a number-average molecular weight ($M_n$) between 300 and 5000 Daltons (Da), such as PPG425, PPG1000, and PPG2000. In embodiments, the stabilizing excipients can comprise a PPG/PEG copolymer with up to 50% of polyethylene glycol (PEG) repeating units. A PPG excipient can be a linear polymer with two or three terminal hydroxyl groups. In embodiments, the stabilizing excipients can comprise a polypropylene glycol (PPG) adduct, such as a reaction product between propylene glycol and an alcohol group or an amine group. In embodiments, the PPG excipient can be in the form of a branched polymer formed by addition of propylene glycol units to a branched or multifunctional alcohol or amine like glycerol, triethanolamine, a sugar, or pentaerythritol.

In embodiments, the stabilizing excipient can comprise a hydrophobically modified cellulose such as hydroxypropyl methylcellulose, methylcellulose, hydroxypropyl cellulose, or hydroxyethyl cellulose. Low molecular weight hydroxypropyl methylcellulose (HPMC) and low molecular weight methylcellulose (MC) are commercially available under the trademark METHOCEL® from Dow Chemical Company (Midland, Mich.). The naming convention for the Methocel product line is such that the number in the product name is the viscosity of a 2% solution in water, "LV" stands for low viscosity, and the first letter indicates the type (HPMC or MC) and degree of substitution. Low molecular weight HPMC products such as Methocel E3LV, Methocel E15LV and Methocel K3LV and low molecular weight MC products (e.g. Methocel A15LV) can be used as stabilizing excipients.

In embodiments, the stabilizing excipient can comprise a polyvinyl alcohol that is prepared from polyvinyl acetate with a molecular weight between 5000 and 500,000 Da and a degree of hydrolysis between 50% and 100%. In embodiments, the polyvinyl alcohol has a degree of hydrolysis from 80% to about 99%, or from about 83% to about 95%. In embodiments, the polyvinyl alcohol has a molecular weight between about 10,000 and about 100,000 Da. In embodiments, the polyvinyl alcohol has a 4% aqueous solution viscosity at 20-25° C. in the range of about 3 to about 50 cP. In embodiments, the polyvinyl alcohol is a United States Pharmacopeia (USP) grade.

In embodiments, the stabilizing excipient can comprise a polyvinylpyrrolidone (PVP). The PVP excipient can have a molecular weight of about 1000 to about 1.5 million Da. In embodiments, the PVP stabilizing excipient can have a molecular weight of about 5000 to about 200,000 Da. In embodiments, the PVP stabilizing excipient can have a molecular weight of about 10,000 to about 100,000 Da.

In embodiments, the stabilizing excipient can comprise a polyoxazoline such as poly(2-methyl-2-oxazoline), poly(2-ethyl-2-oxazoline) or poly(2-propyl-2-oxazoline). In embodiments, the stabilizing polyoxazoline excipient can have a number-average molecular weight of 1,000 to 500,000 Da or 5,000 to 50,000 Da.

The stabilizing excipient can be added alone, or in combination with conventional surfactants such as nonionic surfactants such as Polysorbate 80, Polysorbate 20 and the like. When a stabilizing excipient is combined with a conventional surfactant excipient, a lesser amount of conventional excipient may be required, for example. 0-100 ppm of the conventional surfactant, or 100-2000 ppm of the conventional surfactant. In other embodiments, the therapeutic protein formulation contains the stabilizing excipient and an amount of 10-5000 ppm of a conventional surfactant. In embodiments, the stabilizing excipient is added to the formulation in amounts ranging from 10-5000 ppm. In embodiments, the stabilizing excipient is added to the formulation in amounts ranging from 100-1000 ppm. Reducing the amounts of conventional surfactant in a therapeutic formulation can offer certain advantages such as improved formulation stability, improved excipient stability, and reduced foaming tendency. In embodiments, solutions of therapeutic proteins containing the stabilizing excipients of the invention can have a lower foaming tendency compared with solutions of the same therapeutic proteins without the stabilizing excipients.

Advantageously, the stabilizing excipients can be selected so that they do not form micelles in aqueous solution and they can pass through an ultrafiltration membrane. Advantageously, the stabilizing excipients can be selected so that they do not increase the foaming tendency of the formulation. Advantageously, the stabilizing excipients can be selected so that they do not include conventional amphiphilic surfactant structures. In embodiments, the stabilizing excipients can be selected so that they are not structured as having a hydrophilic head and a hydrophobic tail. In other embodiments, the stabilizing excipients can be selected so that they do not comprise block copolymers, for example, so that block copolymer arrangements such as the (propylene oxide-co-ethylene oxide) copolymer configurations of PO/EO/PO, EO/PO or EO/PO/EO are excluded. In embodiments, stabilizing excipients can be selected that are free of ethylene oxide (EO) groups, residual ethylene oxide monomer, and/or dioxane byproducts. In embodiments, the stabilizing excipients are selected so that they contain no ester linkages. In embodiments, the stabilizing excipients are purified to minimize the presence of endotoxins or heavy metals. In embodiments, the stabilizing excipients are USP grade materials. Stabilizing excipient compounds as disclosed herein can be natural or synthetic, and, in certain embodiments they may be substances that the U.S. FDA generally recognizes as safe (GRAS), or that are well established and commonly used in registered drug products such as are usually included in pharmacopoeias, or that are included in a registry or database such as the FDA's Inactive Ingredient Database (https://www.accessdata.fda.gov/scripts/cder/iig/).

3. Therapeutic Formulations

In one aspect, the formulations and methods disclosed herein provide stable liquid formulations, comprising a therapeutic protein in a therapeutically effective amount and a stabilizing excipient compound. In embodiments, the formulation can improve the stability while providing an acceptable concentration of active ingredients and an acceptable stability. In embodiments, the formulation provides an improvement in stability when compared to a control formulation; for the purposes of this disclosure, a control formulation is a formulation containing the protein active ingredient that is identical on a dry weight basis in every way to the therapeutic formulation except that it lacks the excipient compound. In embodiments, improved stability of the protein containing formulation is indicated by a lower percentage of soluble aggregates, a lower percentage of fragments, a decrease in the number of particulates, a decrease in the number of subvisible particles, a decrease in the hydrodynamic particle size, or the suppression of gel formation, as compared to a control formulation after a stress condition. In embodiments, the stress conditions can include freeze/thaw cycles, exposure to storage conditions for >1 month at freezing temperatures (below 0° C.), exposure to storage conditions for >1 month at refrigerated temperatures (between 0° C. and 15° C.), exposure to storage conditions for >1 month at ambient temperatures (between 15° C. and 30° C.), exposure to storage conditions for >1 week at elevated temperatures (between 30° C. and 100° C.), exposure to agitation stress, exposure to air/water interfaces, contact with plastic, glass, or metal surfaces, filtration, column chromatography separation, viral inactivation, exposure to pH conditions between pH 2 and pH 5, exposure to pH conditions between pH 8 and pH 12, exposure to proteolytic enzymes, exposure to lipase enzymes, or exposure to microbiological contamination.

It is understood that the stability of a liquid protein formulation can be affected by a variety of factors, including, but not limited to: the nature of the protein itself (e.g., enzyme, antibody, receptor, fusion protein, etc.); its size, three-dimensional structure, chemical composition, and molecular weight; its concentration in the formulation; the components of the formulation besides the protein; the formulation pH range; the storage conditions for the formulation; and the method of administering the formulation to the patient. Therapeutic proteins most suitable for use with the excipient compounds described herein are preferably essentially pure, i.e., free from contaminating proteins. In embodiments, an "essentially pure" therapeutic protein is a protein composition comprising at least 90% by weight of the therapeutic protein, or preferably at least 95% by weight, or more preferably, at least 99% by weight, all based on the total weight of therapeutic proteins and contaminating proteins in the composition. For the purposes of clarity, a protein added as an excipient is not intended to be included in this definition. The therapeutic formulations described herein are intended for use as pharmaceutical-grade formulations, i.e., formulations intended for use in treating a mammal, in such a form that the desired therapeutic efficacy of the protein active ingredient can be achieved, and without containing components that are toxic to the mammal to whom the formulation is to be administered.

In embodiments, the therapeutic formulation contains at least 1 µg/mL of protein active ingredient. In embodiments, the therapeutic formulation contains between about 1 µg/mL and about 1 mg/mL of protein active ingredient. In embodiments, the therapeutic formulation contains at least 1 mg/mL of protein active ingredient. In embodiments, the therapeutic formulation contains at least 5 mg/mL of protein active ingredient. In other embodiments, the therapeutic formulation contains at least 100 mg/mL of protein active ingredient. In other embodiments, the therapeutic formulation contains at least 200 mg/mL of protein active ingredient. In yet other embodiments, the therapeutic formulation solution contains at least 300 mg/mL of protein active ingredient. Generally, the excipient compounds disclosed herein are added to the therapeutic formulation in an amount between about 1 to about 5000 ppm. In embodiments, the excipient compound can be added in an amount of about 1 to about 500 ppm. In embodiments, the excipient compound can be added in an amount of about 10 to about 100 ppm.

In embodiments, the excipient compounds disclosed herein are added to the therapeutic formulation in a stability-improving amount. In embodiments, a stability-improving amount is the amount of an excipient compound that reduces the degradation of the formulation by at least 10% when compared to a control formulation; for the purposes of this disclosure, a control formulation is a formulation containing the protein active ingredient that is identical on a dry weight basis in every way to the therapeutic formulation except that it lacks the excipient compound. In embodiments, the stability-improving amount is the amount of an excipient compound that reduces the degradation of the formulation by at least 30% when compared to the control formulation. In embodiments, the stability-improving amount is the amount of an excipient compound that reduces the degradation of the formulation by at least 50% when compared to the control formulation. In embodiments, the stability-improving amount is the amount of an excipient compound that reduces the degradation of the formulation by at least 70% when compared to the control formulation. In embodiments, the stability-improving amount is the amount of an excipient compound that reduces the degradation of the formulation by at least 90% when compared to the control formulation.

Therapeutic formulations in accordance with this disclosure have certain advantageous properties. In embodiments, the therapeutic formulations are resistant to shear degradation, phase separation, clouding out, precipitation, and denaturing. In embodiments, the therapeutic formulations are processed, purified, stored, syringed, dosed, filtered, and centrifuged more effectively, compared with a control formulation. In embodiments, the therapeutic formulations can result in fewer adverse infusion-related effects, for example, adverse infusion reactions, adverse immunogenic responses, decrease in half-life of a therapeutic protein in the therapeutic formulation, and the like. In embodiments, when the therapeutic formulations are administered to patients, they can experience fewer infusion reactions than would be experienced with a similar formulation lacking the stabilizing excipient. In embodiments, when the therapeutic formulations are administered to patients, they can experience fewer or less intense immunogenic responses than would be experienced with a similar formulation lacking the stabilizing excipient. In embodiments, when the therapeutic formulations are administered to patients, they can experience less decrease in the half-life of the therapeutic protein in the body, as compared to a similar formulation lacking the stabilizing excipient.

In embodiments, the stabilizing excipient has antioxidant properties that stabilize the therapeutic protein against oxidative damage. In embodiments, the therapeutic formulation is stored at ambient temperatures, or for extended time at refrigerator conditions without appreciable loss of potency for the therapeutic protein. In embodiments, the therapeutic formulation is dried down for storage until it is needed; then it is reconstituted with an appropriate solvent, e.g., water. Advantageously, the formulations prepared as described herein can be stable over a prolonged period of time, from months to years. When exceptionally long periods of storage are desired, the formulations can be preserved in a freezer (and later reactivated) without fear of protein denaturation. In embodiments, formulations can be prepared for long-term storage that do not require refrigeration. In embodiments, the stabilizing excipient can be used to improve solubility or stability of protein therapeutics that have limited water solubility, such as antibody-drug conjugates.

In embodiments, the stabilizing excipient provides a substitute for some or all of the conventional surfactants that are employed in protein formulations, as described previously. As described previously, the stabilizing excipient can be added to a protein formulation alone or in combination with one or more other excipients, either to replace the conventional surfactant in the formulation entirely, or to reduce the amount of the conventional surfactant that is used. In embodiments, the stabilizing excipient is not an ethoxylated compound, and does not contain residual amounts of 1,4-dioxane.

Methods for preparing therapeutic formulations may be familiar to skilled artisans. The therapeutic formulations of the present invention can be prepared, for example, by adding the stabilizing excipient compound to the formulation before or after the therapeutic protein is added to the solution. The therapeutic formulation can, for example, be produced by combining the therapeutic protein and the excipient at a first (lower) concentration and then processed by filtration or centrifugation to produce a second (higher) concentration of the therapeutic protein. Therapeutic formulations can be made with one or more of the excipient compounds with chaotropes, kosmotropes, hydrotropes, and salts. Therapeutic formulations can be made with one or more of the excipient compounds using techniques such as encapsulation, dispersion, liposome, vesicle formation, and the like. Methods for preparing therapeutic formulations comprising the stabilizing excipient compounds disclosed herein can include combinations of the excipient compounds. Other additives may be introduced into the therapeutic formulations during their manufacture, including preservatives, conventional surfactants, sugars, sucrose, trehalose, polysaccharides, arginine, proline, hyaluronidase, stabilizers, buffers, and the like. As used herein, a pharmaceutically acceptable stabilizing excipient compound is one that is non-toxic and suitable for animal and/or human administration.

4. Protein/Excipient Formulations: Properties and Processes

In embodiments, certain of the above-described stabilizing excipient compounds are used to improve a protein-related process, such as the manufacture, processing, sterile filling, purification, and analysis of protein-containing solutions, using processing methods such as filtration, syringing, transferring, pumping, mixing, heating or cooling by heat transfer, gas transfer, centrifugation, chromatography, membrane separation, centrifugal concentration, tangential flow filtration, radial flow filtration, axial flow filtration, lyophilization, and gel electrophoresis. These processes and processing methods can have improved efficiency due to the improved stability of the proteins in the solution during manufacture, processing, purification, and analysis steps. In embodiments, the stabilizing excipient can be added to a protein-containing solution before a concentration step, and the stabilizing excipient can improve the efficiency, throughput, or yield of the concentration step. In embodiments, the stabilizing excipient does not become concentrated with the protein phase during a filtration-based concentration step. In embodiments, the stabilizing excipient does not form micelles when added to a protein-containing solution. Additionally, equipment-related processes such as the cleanup, sterilization, and maintenance of protein processing equipment can be facilitated by the use of the above-identified excipients due to decreased fouling, decreased denaturing, lower viscosity, and improved solubility of the protein.

EXAMPLES

As used herein, the term wt % refers to percentage on a weight basis.

Example 1: Agitation Stress of ERBITUX® Formulations

This example compares the effect of the following stabilizing excipients in ERBITUX® formulations that were subjected to agitation stresses: polypropylene glycol, $M_n$~425 g/mol (PPG425), polypropylene glycol, $M_n$~1000 g/mol (PPG1000), polypropylene glycol, $M_n$~2000 g/mol (PPG2000), polyethylene glycol, $M_n$~1000 g/mol (PEG1000). All stabilizing excipient reagents were obtained from Sigma-Aldrich, St. Louis, Mo.

An ERBITUX® formulation was prepared as follows. A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate.

The ERBITUX® sample was then reformulated in 15 mM sodium phosphate and 4.8 mg/mL sodium chloride at pH 7 in the presence of about 200 ppm of a stabilizing excipient in the following way. Buffer solutions were prepared by dissolving approximately 0.1 g sodium phosphate monobasic dihydrate (Sigma-Aldrich, St. Louis, Mo.), 0.24 g sodium chloride (Sigma-Aldrich, St. Louis, Mo.) and about 0.1 g of the desired stabilizing excipient in deionized water, and diluted to a final mass of about 50 g with additional deionized water. The solution pH of each buffer was adjusted to about 7 with the dropwise addition of either 5 M sodium hydroxide or 1 M sodium hydroxide. Buffers were filtered through 0.2 micron sterile polyethersulfone syringe filter (GE Healthcare Biosciences, Pittsburgh, Pa.), and 0.4 mL of each buffer added to sterile 5 mL polypropylene tubes along with about 3.4 mL of the same buffer containing no excipient. In this way, a final excipient concentration of about 200 ppm was achieved in each sample. Amicon Ultra 15 centrifugal concentrator tubes with a 30 kDa nominal molecular weight cut-off (EMD-Millipore, Billerica, Mass.) were rinsed with deionized water, filled with 13 mL of Erbitux sample, and centrifuged in a Sorvall Legend RT centrifuge for about 25 minutes at about 3200×g and 25° C. to a final retentate volume of about 1 mL or a concentration of about 30 mg/mL cetuximab. The filtrate was then removed and about 0.26 mL was added to each buffer containing 5 mL sterile polypropylene tube, filtered through 0.2 micron sterile syringe filters.

The resulting cetuximab formulations in the 5 mL polypropylene tubes, having a concentration of about 2 mg/mL cetuximab and final volume of about 4 mL, were placed on a Daigger Scientific (Vernon Hills, Ill.) Labgenius orbital shaker at 275 rpm for agitation stressing. After about 16 hours and about 40 hours of continuous shaking at ambient temperature, samples were pulled and analyzed by optical absorbance in a Thermo Fisher Scientific Evolution spectrophotometer with a 10 mm path length cuvette, and by dynamic light scattering (DLS) with a ZetaPlus from Brookhaven Instruments (Holtsville, N.Y.).

Absorbance at 350 nm and 550 nm was utilized as a measurement of turbidity, with higher absorbance indicating more degradation of the cetuximab after stress, due to the formation of more insoluble particulates. Absorbance values are reported in Absorbance Units (AU) from the spectrophotometer measurements. The results are presented in Table 1 below, showing absorbance values measured after 0, 16, and 40 hours of agitation.

Dynamic light scattering (DLS) measurements yielded an effective diameter in nanometers and were not corrected for slight differences in viscosity and refractive index of the buffers. Instead, the DLS measurements were used as a more sensitive way than turbidity for monitoring protein aggregation. The DLS results are summarized in Table 2.

TABLE 1

| Stabilizing excipient | Absorbance at 350 nm (AU) | | | Absorbance at 550 nm (AU) | | |
|---|---|---|---|---|---|---|
| | 0 hrs | 16 hrs | 40 hrs | 0 hrs | 16 hrs | 40 hrs |
| PEG1000 | −0.01 | 0.00 | 0.01 | −0.02 | −0.01 | −0.01 |
| PPG425 | −0.01 | −0.03 | −0.04 | −0.02 | −0.03 | −0.04 |
| PPG1000 | −0.03 | −0.02 | 0.00 | −0.03 | −0.02 | 0.00 |
| PPG2000 | −0.04 | −0.03 | −0.01 | −0.04 | −0.03 | −0.01 |
| None | −0.01 | 0.91 | 1.62 | −0.01 | 0.52 | 0.96 |

TABLE 2

| Stabilizing excipient | DLS effective diameter (nm) | | |
|---|---|---|---|
| | 0 hrs | 16 hrs | 40 hrs |
| PEG1000 | 11.6 | 14.2 | 2900 |
| PPG425 | 11.8 | 12.0 | 11.8 |
| PPG1000 | 11.8 | 11.5 | 11.7 |
| PPG2000 | 11.6 | 12.2 | 12.1 |
| None | 11.6 | 1729 | 1248 |

The four formulations containing a stabilizing excipient all performed substantially better than the control formulation (which used the same buffer with no excipient). There was no significant difference in light absorbance measurements for the four formulations containing excipient. However, DLS measurements of effective particle diameter indicated aggregate formation in the sample containing PEG1000, while the samples containing PPG did not show any signs of aggregation, regardless of molecular weight within the range tested in this example. Therefore, in can be concluded that the various PPG excipients are more effective in preventing degradation of protein solutions due to agitation and/or exposure to air/liquid interfaces than PEG1000.

Example 2: FlowCAM Particle Analysis of Stressed Cetuximab Formulations

Samples containing about 2 mg/mL cetuximab in phosphate buffer at pH 7 with 200 ppm excipient, prepared in accordance with Example 1, were analyzed for insoluble particles by dynamic flow imaging with a FlowCam VS1 (Fluid Imaging Technologies, Scarborough, Me.). The FlowCam was equipped with a 20× objective lens and a 50 micron depth flow cell, and operated at a flow rate of 0.03 mL/min. Measurements were made in triplicate using a sample volume of 0.2 mL per run. Particles were counted and grouped into four categories by equivalent spherical diameter using the VisualSpreadsheet particle analysis software provided with the FlowCam instrument, and each particle class averaged for the three sample runs. The results of the experiment are presented in Table 3 below. Particle analysis by FlowCam further demonstrated the greater stabilization achieved with PPG excipients than the PEG1000. Within the PPG samples, PPG1000 and PPG2000 performed similarly and yielded slightly lower particle counts than the sample with PPG425 as the excipient.

TABLE 3

| | Average number of particles per mL after 40 hours shaking: | | | | | | | |
|---|---|---|---|---|---|---|---|---|
| | 2-10 μm particles | | 10-20 μm particles | | 20-50 μm particles | | >50 μm particles | |
| Stabilizing excipient | Avg. | St. Dev. | Avg. | St. Dev. | Avg. | St. Dev. | Avg. | St. Dev. |
| PEG1000 | 129445 | 14028 | 18474 | 988 | 9055 | 1174 | 1390 | 119 |
| PPG425 | 2119 | 841 | 281 | 139 | 118 | 42 | 22 | 15 |
| PPG1000 | 416 | 103 | 31 | 0 | 0 | 0 | 0 | 0 |
| PPG2000 | 187 | 155 | 21 | 15 | 0 | 0 | 0 | 0 |

Example 3: Evaluation of Low Molecular Weight Hydrophobically Modified Cellulose Low molecular weight hydroxypropyl methylcellulose (HPMC) and low molecular weight methylcellulose (MC) are hydrophobically modified cellulose polymers that are commercially available under the trademark METHOCEL® from Dow Chemical Company (Midland, Mich.). The naming convention for the METHOCEL® product line is such that the number in the product name is the viscosity of a 2% solution in water, "LV" stands for low viscosity, and the first letter indicates the type (HPMC or MC) and degree of substitution. Three low molecular weight HPMC products (Methocel E3LV, Methocel E15LV and Methocel K3LV) and one low molecular weight MC product (Methocel A15LV) were used as stabilizing excipients in this Example along with Polysorbate 80 (PS80) and polypropylene glycol 2000 (PPG2000) which were obtained from Sigma-Aldrich, St. Louis, Mo.

An ERBITUX® formulation was prepared as follows. A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate.

The Erbitux sample was then reformulated in 15 mM sodium phosphate and 4.8 mg/mL sodium chloride at pH 7 in the presence of about 200 ppm of a stabilizing excipient in the following way. Buffer solutions were prepared by dissolving approximately 0.1 g sodium phosphate monobasic dihydrate (Sigma-Aldrich, St. Louis, Mo.), 0.24 g sodium chloride (Sigma-Aldrich, St. Louis, Mo.) and about 0.1 g of the desired stabilizing excipient in deionized water, and diluted to a final mass of about 50 g with additional deionized water. The solution pH of each buffer was adjusted to about 7 with the dropwise addition of either 5 M sodium hydroxide or 1 M sodium hydroxide. Buffers were filtered through 0.2 micron sterile polyethersulfone syringe filter (GE Healthcare Biosciences, Pittsburgh, Pa.), and 0.4 mL of each buffer added to sterile 5 mL polypropylene tubes along with about 3.4 mL of the same buffer containing no excipient. In this way, a final excipient concentration of about 200 ppm was achieved in each sample. Amicon Ultra 15 centrifugal concentrator tubes with a 30 kDa nominal molecular weight cut-off (EMD-Millipore, Billerica, Mass.) were rinsed with deionized water, filled with 13 mL of Erbitux sample, and centrifuged in a Sorvall Legend RT centrifuge for about 27 minutes at about 3200×g and 25° C. to a final retentate volume of about 0.6 mL or a concentration of about 40 mg/mL cetuximab. The filtrate was then removed and about 0.2 mL was added to each buffer containing 5 mL sterile polypropylene tube, filtered through 0.2 micron sterile syringe filters.

The resulting cetuximab formulations in the 5 mL polypropylene tubes, having a concentration of about 2 mg/mL cetuximab and final volume of about 4 mL, were placed on a Daigger Scientific (Vernon Hills, Ill.) Labgenius orbital shaker at 275 rpm. After about 16 hours and about 40 hours of continuous shaking at ambient temperature, samples were pulled and analyzed by light absorbance in a Thermo Fisher Scientific Evolution spectrophotometer with a 10 mm path length cuvette, and by dynamic light scattering (DLS) with a ZetaPlus from Brookhaven Instruments (Holtsville, N.Y.).

Absorbance at 350 nm and 550 nm was utilized as a measurement of turbidity, with higher absorbance indicating more degradation of the cetuximab after stress, due to the formation of more insoluble particulates. The absorbance results are reported in Absorbance Units (AU) from the spectrophotometer measurements and they are summarized in Table 4 below.

Dynamic light scattering measurements yielded an effective diameter in nanometers and were not corrected for slight differences in viscosity and refractive index of the buffers. Instead, the DLS measurements were used as a more sensitive way than turbidity for monitoring protein aggregation. The dynamic light scattering results are summarized in Table 5 below.

TABLE 4

| Stabilizing excipient | Absorbance at 350 nm (AU) | | | Absorbance at 550 nm (AU) | | |
|---|---|---|---|---|---|---|
| | 0 hrs | 16 hrs | 40 hrs | 0 hrs | 16 hrs | 40 hrs |
| Methocel K3LV | −0.01 | 0.01 | −0.08 | −0.01 | 0.01 | −0.09 |
| Methocel E3LV | −0.01 | 0.10 | −0.06 | −0.01 | 0.10 | −0.07 |
| Methocel E15LV | 0.01 | 0.00 | −0.06 | 0.00 | 0.00 | −0.06 |
| Methocel A15LV | −0.02 | −0.01 | −0.07 | −0.02 | −0.01 | −0.07 |
| PS80 | −0.01 | 0.00 | −0.04 | −0.01 | −0.01 | −0.04 |
| PPG2000 | 0.01 | 0.02 | −0.04 | 0.01 | 0.01 | −0.04 |

TABLE 5

| Stabilizing excipient | DLS effective diameter (nm) | | |
|---|---|---|---|
| | 0 hrs | 16 hrs | 40 hrs |
| Methocel K3LV | 12.2 | 12.1 | 12.1 |
| Methocel E3LV | 11.6 | 12.0 | 12.3 |
| Methocel E15LV | 11.8 | 12.3 | 11.9 |
| Methocel A15LV | 12.2 | 12.7 | 11.9 |
| PS80 | 11.7 | 12.3 | 12.3 |
| PPG2000 | 11.9 | 12.5 | 11.6 |

Light absorbance and DLS measurements of samples after exposure to vigorous shear indicate that low molecular weight HPMC and MC was able to protect cetuximab from degrading to the same extent as PS80 and PPG2000.

Example 4: FlowCAM Analysis of Stressed Cetuximab Formulations

Samples containing about 2 mg/mL cetuximab in phosphate buffer at pH 7 with 200 ppm excipient prepared in accordance with Example 3 were analyzed for insoluble particles by dynamic flow imaging using a FlowCam VS1 (Fluid Imaging Technologies, Scarborough, Me.). The FlowCam was equipped with a 20× objective lens and a 50 micron depth flow cell, and operated at a flow rate of 0.03 mL/min. Measurements were made in duplicate using a sample volume of 1.0 mL per run. Particles were counted and grouped into four categories by equivalent spherical diameter using the VisualSpreadsheet particle analysis software provided with the FlowCam instrument, with the reported value for each particle class being an average from the two sample runs. The results are set forth in Table 6 below.

TABLE 6

| | Average number of particles per mL after 40 hours shaking: | | | | | | | |
|---|---|---|---|---|---|---|---|---|
| | 2-10 μm particles | | 10-20 μm particles | | 20-50 μm particles | | >50 μm particles | |
| Stabilizing excipient | Avg. | St. Dev. | Avg. | St. Dev. | Avg. | St. Dev. | Avg. | St. Dev. |
| Methocel K3LV | 2564 | 640 | 309 | 46 | 113 | 3 | 0 | 0 |
| Methocel E3LV | 893 | 39 | 46 | 15 | 9 | 3 | 0 | 0 |
| Methocel E15LV | 1773 | 328 | 481 | 7 | 86 | 18 | 0 | 0 |
| Methocel A15LV | 2021 | 93 | 145 | 28 | 31 | 6 | 0 | 0 |
| PS80 | 383 | 32 | 31 | 13 | 6 | 6 | 0 | 0 |
| PPG2000 | 493 | 56 | 15 | 9 | 0 | 0 | 0 | 0 |

Example 5: Testing of PPG and PEG as Stabilizing Excipients

This example compares the effect of the following additives as stabilizing excipients: propylene glycol (PG), dipropylene glycol (DPG), tripropylene glycol (TPG), polypropylene glycol, $M_n$~425 g/mol (PPG425), polypropylene glycol, $M_n$~725 g/mol (PPG725), polyethylene glycol, $M_n$~400 g/mol (PEG400), and Polysorbate 80 (PS80).

An ERBITUX® formulation was prepared as follows. A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate.

The ERBITUX® sample was then reformulated in 15 mM sodium phosphate and 4.8 mg/mL sodium chloride at pH 7 in the presence of about 200 ppm stabilizing excipient in the following way. Buffer solutions were prepared by dissolving approximately 0.1 g sodium phosphate monobasic dihydrate (Sigma-Aldrich, St. Louis, Mo.), 0.24 g sodium chloride (Sigma-Aldrich, St. Louis, Mo.) and about 0.01 g of the desired stabilizing excipient in deionized water, and diluted to a final mass of about 50 g with additional deionized water. The solution pH of each buffer was adjusted to about 7 with the dropwise addition of either 5 M sodium hydroxide or 1 M sodium hydroxide. Buffers were filtered through 0.2 micron sterile polyethersulfone syringe filter (GE Healthcare Biosciences, Pittsburgh, Pa.), and 3.8 mL of each buffer added to sterile 5 mL polypropylene tubes. Amicon Ultra 15 centrifugal concentrator tubes with a 30 kDa nominal molecular weight cut-off (EMD-Millipore, Billerica, Mass.) were rinsed with deionized water, filled with 14 mL of Erbitux sample, and centrifuged in a Sorvall Legend RT centrifuge for about 25 minutes at about 3200×g and 25° C. to a final retentate volume of about 1 mL or a concentration of about 30 mg/mL cetuximab. The filtrate was then removed and about 0.27 mL was added to each buffer containing 5 mL sterile polypropylene tube, filtered through 0.2 micron sterile syringe filters.

The resulting cetuximab formulations in the 5 mL polypropylene tubes, having a concentration of about 2 mg/mL cetuximab and final volume of about 4 mL, were placed on a Daigger Scientific (Vernon Hills, Ill.) Labgenius orbital shaker at 275 rpm. After 16 hours and 39 hours of continuous shaking at ambient temperature, samples were analyzed by light absorbance in a Thermo Fisher Scientific Evolution spectrophotometer with a 10 mm path length cuvette, and by dynamic light scattering (DLS) with a ZetaPlus from Brookhaven Instruments (Holtsville, N.Y.).

Absorbance at 350 nm and 550 nm was utilized as a measurement of turbidity, with higher absorbance indicating more degradation of the product due to the formation of more insoluble particulates. Absorbance values are reported in Absorbance Units (AU) from the spectrophotometer measurements. These results are presented in Table 7.

Light scattering measurements yielded an effective diameter in nanometers and Instead, the DLS measurements were used as a more sensitive way to monitor aggregation of the protein than turbidity. The DLS results are summarized in Table 8.

TABLE 7

| Test No. | Stabilizing Excipient | Absorbance at 350 nm (AU) | | | Absorbance at 550 nm (AU) | | |
|---|---|---|---|---|---|---|---|
| | | 0 hrs | 16 hrs | 39 hrs | 0 hrs | 16 hrs | 39 hrs |
| 5.1 | PPG425 | −0.006 | −0.007 | −0.019 | −0.002 | −0.005 | −0.017 |
| 5.2 | PS80 | −0.025 | −0.005 | −0.013 | −0.019 | −0.002 | −0.016 |
| 5.3 | PEG400 | −0.026 | 0.072 | 0.395 | −0.019 | 0.044 | 0.192 |
| 5.4 | PG | −0.018 | 0.156 | 0.53 | −0.013 | 0.089 | 0.303 |
| 5.5 | DPG | −0.023 | 0.355 | 0.671 | −0.019 | 0.192 | 0.366 |
| 5.6 | TPG | 0.052 | 0.184 | 0.594 | 0.055 | 0.104 | 0.328 |
| 5.7 | PPG725 | −0.015 | −0.008 | −0.034 | −0.012 | 0.005 | −0.033 |

TABLE 8

| Test No. | Stabilizing Excipient | DLS Effective Diameter (nm) | | |
|---|---|---|---|---|
| | | 0 hrs | 16 hrs | 39 hrs |
| 5.1 | PPG425 | 11.6 | 11.8 | 11.5 |
| 5.2 | PS80 | 11.9 | 11.5 | 11.7 |
| 5.3 | PEG400 | 11.7 | 4430 | 2313 |
| 5.4 | PG | 11.4 | 3942 | 1697 |
| 5.5 | DPG | 11.6 | 6182 | 2077 |
| 5.6 | TPG | 11.4 | 4691 | 2463 |
| 5.7 | PPG725 | 11.5 | 11.6 | 11.7 |

Results from light absorbance and DLS particle size demonstrate that polypropylene glycol was more effective in preventing aggregation of cetuximab after severe agitation and high exposure to air/liquid interface than polyethylene glycol of a similar molecular weight. Polypropylene glycol also demonstrated better performance than propylene glycol or its dimer or trimer. Polypropylene glycol and polysorbate 80 had similar absorbance and DLS results.

Example 6: Testing of Stabilizing Excipients

This example compares the effect of the following additives as stabilizing excipients: hydroxypropyl methylcellulose, $M_n$~10,000 (HPMC), PPG425, acesulfame K, saccharin, leucine, and sodium propionate (Na Propionate).

An ERBITUX® formulation was prepared as follows. A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate.

The ERBITUX® sample was then reformulated in 15 mM sodium phosphate at pH 7 in the presence of various stabilizing excipients in the following way. Buffer solutions containing excipients were prepared by dissolving approximately 0.1 g sodium phosphate monobasic dihydrate (Sigma-Aldrich, St. Louis, Mo.) and the desired excipients in deionized water and adjusting the pH of the solution to 7 with the dropwise addition of either 1 M sodium hydroxide or 1 M hydrochloric acid. Solutions were diluted to a final volume of 50 mL in a volumetric flask with additional deionized water. Buffers were filtered through 0.2 micron sterile polyethersulfone syringe filter (GE Healthcare Biosciences, Pittsburgh, Pa.), and 3.8 mL of each buffer added to sterile 5 mL polypropylene tubes. Amicon Ultra 15 centrifugal concentrator tubes with a 30 kDa nominal molecular weight cut-off (EMD-Millipore, Billerica, Mass.) were rinsed with deionized water, filled with 14 mL of Erbitux sample, and centrifuged in a Sorvall Legend RT centrifuge for about 25 minutes at about 3200×g and 25° C. to a final retentate volume of about 1 mL or a concentration of about 30 mg/mL cetuximab. The filtrate was then removed and about 0.28 mL was added to each buffer containing 5 mL sterile polypropylene tube, filtered through 0.2 micron sterile syringe filters.

The resulting cetuximab formulations in the 5 mL polypropylene tubes, having a concentration of about 2 mg/mL and final volume of about 4 mL, were placed on a Daigger Scientific (Vernon Hills, Ill.) Labgenius orbital shaker at 275 rpm. After 16 hours and 36 hours of continuous shaking at ambient temperature, samples were analyzed by optical absorbance in a Thermo Fisher Scientific Evolution spectrophotometer with a 10 mm path length cuvette and by dynamic light scattering (DLS) with a ZetaPlus from Brookhaven Instruments (Holtsville, N.Y.).

Absorbance at 350 nm and 550 nm was utilized as a measurement of turbidity, with higher absorbance indicating more degradation of the product after stress, due to the formation of more insoluble particulates. Absorbance values are reported in Absorbance Units (AU) from the spectrophotometer measurements. In some cases, samples were allowed to shake for a total of 128 hours and absorbance measurements obtained. The results are presented in Table 9 below.

Dynamic light scattering (DLS) measurements yielded an effective diameter in nanometers and were not corrected for slight differences in viscosity and refractive index of the buffers. Instead, the DLS measurements were used as a more sensitive way than turbidity for monitoring protein aggregation. The results are summarized in Table 10 below.

TABLE 9

| Test No. | Excipient 1 Name | Conc. (g/50 mL) | Excipient 2 Name | Conc. (g/50 mL) | ABS 350 nm (AU) 0 hrs | ABS 350 nm (AU) 16 hrs | ABS 350 nm (AU) 36 hrs | ABS 550 nm (AU) 0 hrs | ABS 550 nm (AU) 16 hrs | ABS 550 nm (AU) 36 hrs |
|---|---|---|---|---|---|---|---|---|---|---|
| 6.1 | HPMC | 0.2 | NaCl | 0.23 | 0.00 | 0.01 | 0 | −0.01 | 0.00 | 0.00 |
| 6.2 | KS | 0.75 | NaCl | 0.23 | 0.00 | 0.11 | 0.15 | −0.02 | 0.06 | 0.07 |
| 6.3 | LBA | 0.75 | NaCl | 0.23 | 0.02 | 0.04 | 1.15 | −0.03 | 0.02 | 0.72 |
| 6.4 | PPG425 | 0.42 | NaCl | 0.23 | 0.02 | 0.04 | 0.01 | −0.03 | 0.04 | 0.02 |
| 6.5 | Acesulfame K | 0.75 | NaCl | 0.23 | 0.02 | 0.13 | 1.01 | 0.02 | 0.07 | 0.59 |
| 6.6 | Saccharin | 0.75 | NaCl | 0.23 | 0.00 | 1.53 | 2.59 | −0.03 | 0.87 | 1.88 |
| 6.7 | Leucine | 0.49 | NaCl | 0.23 | 0.03 | 0.22 | 0.44 | −0.03 | 0.12 | 0.28 |
| 6.8 | Na Propionate | 0.75 | — | — | −0.01 | 0.37 | 1.51 | −0.02 | 0.21 | 0.89 |
| 6.9 | None (Erbitux commercial sample) | — | — | — | −0.02 | 0.63 | 1.17 | −0.02 | 0.37 | 0.67 |

TABLE 10

| | | DLS Effective Diameter (nm) | | | |
|---|---|---|---|---|---|
| Test No. | Excipients | 0 hrs | 16 hrs | 36 hrs | 128 hrs |
| 6.1 | See Table 9 | 14.2 | 14.2 | 15.3 | N/A |
| 6.2 | See Table 9 | 11.9 | 4118 | 4626 | 4098 |
| 6.3 | See Table 9 | 15.3 | 1588 | 7277 | N/A |
| 6.4 | See Table 9 | 11.9 | 12.3 | 12.1 | 12.3 |
| 6.5 | See Table 9 | 11.5 | 4176 | 6121 | N/A |
| 6.6 | See Table 9 | 11.9 | 9192 | 3303 | N/A |
| 6.7 | See Table 9 | 11.9 | 7363 | 4674 | 4326 |
| 6.8 | See Table 9 | 12.6 | 3936 | 3902 | N/A |
| 6.9 | See Table 9 | 11.5 | 6055 | 8840 | N/A |

An Agilent 1100 series HPLC with auto-sampler was employed to conduct size-exclusion chromatography (SEC) analysis of the above formulations to monitor loss of cetuximab monomer after exposure to shaking stress. Samples were run on a TSKgel Super SW3000 4.6 mm×30 cm column (Tosoh Bioscience) with an injection volume of 15 microliters and a flow rate of 0.35 mL/min. An Agilent 1100 series diode array detector was used to measure eluate absorbance at 280 nm with a bandwidth of 4 nm. The column temperature was set to 25° C., and the mobile phase was 0.2 M sodium phosphate, pH 6.8. Change in area of the monomer peak before and after stress was used to quantify monomer loss. Monomer peak area after shaking stress was reported as a percentage of the monomer peak area before stress exposure. These results are presented in Table 11 below.

TABLE 11

| | | % monomer retained after shaking | |
|---|---|---|---|
| Test No. | Excipients | 16 hrs | 36 hrs |
| 6.1 | See Table 9 | 100% | 101% |
| 6.2 | See Table 9 | 98% | 99% |
| 6.3 | See Table 9 | 97% | 73% |
| 6.4 | See Table 9 | 99% | 100% |
| 6.5 | See Table 9 | 97% | 86% |
| 6.6 | See Table 9 | 70% | 22% |
| 6.7 | See Table 9 | N/A | N/A |
| 6.8 | See Table 9 | 93% | 73% |
| 6.9 | See Table 9 | 89% | 81% |

Results from light absorbance, DLS particle size and size-exclusion HPLC (SE-HPLC) demonstrate that hydroxypropyl methyl cellulose and polypropylene glycol prevent the aggregation of cetuximab after severe agitation and high exposure to air/liquid interface. In the presence of either excipient, formation of visible particles was prevented, as shown by absorbance data. Preservation of initial monomer size, shown by DLS particle sizing data, indicates suppression of soluble aggregate formation. SE-HPLC corroborates these measurements, demonstrating essentially no loss of monomer in sample.

The formulation with potassium sorbate also showed significant improvement over the commercial ERBITUX® product in suppressing turbidity after shaking.

Example 7: Shaker Stress of Erbitux Formulations with Different Amounts of PPG425

An ERBITUX® formulation was prepared as follows. A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate.

The ERBITUX® sample was then reformulated in 15 mM sodium phosphate and 4.8 mg/mL sodium chloride at pH 7 in the presence of varying amounts of polypropylene glycol having an average molecular weight of about 425 g/mol (PPG425) in the following way. Buffer solutions containing PPG425 were prepared by dissolving approximately 0.1 g sodium phosphate monobasic dihydrate (Sigma-Aldrich, St. Louis, Mo.) and the desired excipients in deionized water and adjusting the pH of the solution to 7 with the dropwise addition of 1 M sodium hydroxide. Solutions were diluted to a final volume of 50 mL in a volumetric flask with additional deionized water. In some cases, a buffer containing no PPG425 was added to a buffer containing PPG425 in such a way as to obtain a buffer with a lower PPG425 concentration with the same phosphate and sodium chloride concentrations at pH about 7. Buffers were filtered through 0.2 micron sterile polyethersulfone syringe filter (GE Healthcare Biosciences, Pittsburgh, Pa.), and 3.8 mL of each buffer added to sterile 5 mL polypropylene tubes. Amicon Ultra 15 centrifugal concentrator tubes with a 30 kDa nominal molecular weight cut-off (EMD-Millipore, Billerica, Mass.) were rinsed with deionized water, filled with 14 mL of Erbitux sample, and centrifuged in a Sorvall Legend RT centrifuge for about 25 minutes at about 3200×g and 25° C. to a final retentate volume of about 1 mL or a concentration of about 30 mg/mL cetuximab. The filtrate was then removed and about 0.28 mL was added to each buffer containing 5 mL sterile polypropylene tube, filtered through 0.2 micron sterile syringe filters.

The resulting cetuximab formulations in the 5 mL polypropylene tubes, having a concentration of about 2 mg/mL cetuximab and final volume of about 4 mL, were placed on a Daigger Scientific (Vernon Hills, Ill.) Labgenius orbital shaker at 275 rpm. After 23 hours and 54 hours of continuous shaking at ambient temperature, samples were analyzed by light absorbance in a Thermo Fisher Scientific Evolution spectrophotometer with a 10 mm path length cuvette and by dynamic light scattering (DLS) with a ZetaPlus from Brookhaven Instruments Corp. (Holtsville, N.Y.).

Absorbance at 350 nm and 550 nm was utilized as a measurement of turbidity, with higher absorbance indicating more degradation of the product after stress in the form of more insoluble particulates. Absorbance values are reported in Absorbance Units (AU) from the spectrophotometer measurements. These results are presented in Table 12 below.

Dynamic light scattering (DLS) measurements yielded an effective diameter in nanometers and were not corrected for slight differences in viscosity and refractive index of the buffers. Instead, the DLS measurements were used as a more sensitive way than turbidity for monitoring protein aggregation. These results are summarized in Table 13 below.

TABLE 12

| Test No. | PPG425 Conc (mg/mL) | ABS 350 nm (AU) | | | ABS 550 nm (AU) | | |
|---|---|---|---|---|---|---|---|
| | | 0 hrs | 23 hrs | 54 hrs | 0 hrs | 23 hrs | 54 hrs |
| 7.1 | 0.5 | −0.03 | −0.04 | −0.02 | −0.02 | −0.03 | −0.01 |
| 7.2 | 1 | −0.02 | −0.04 | 0.00 | −0.01 | −0.03 | 0.00 |
| 7.3 | 2 | −0.03 | −0.04 | 0.01 | −0.03 | −0.02 | 0.01 |
| 7.4 | 5 | −0.03 | −0.04 | 0.04 | −0.02 | −0.02 | 0.05 |

TABLE 13

| Test No. | PPG425 Conc (mg/mL) | DLS Effective Diameter (nm) | | |
|---|---|---|---|---|
| | | 0 hrs | 23 hrs | 54 hrs |
| 7.1 | 0.5 | 11.3 | 11.7 | 11.3 |
| 7.2 | 1 | 11.6 | 11.4 | 11.5 |
| 7.3 | 2 | 11.6 | 11.6 | 11.5 |
| 7.4 | 5 | 11.6 | 11.9 | 11.7 |

An Agilent 1100 series HPLC with auto-sampler was employed to conduct size-exclusion chromatography (SEC) analysis of the above formulations to monitor loss of cetuximab monomer after exposure to shaking stress. Samples were run on a TSKgel Super SW3000 4.6 mm×30 cm column (Tosoh Bioscience) with an injection volume of 15 microliters and a flow rate of 0.35 mL/min. An Agilent 1100 series diode array detector was used to measure eluate absorbance at 280 nm with a bandwidth of 4 nm. The column temperature was set to 25° C., and the mobile phase was 0.2 M sodium phosphate, pH 6.8. Change in area of the monomer peak before and after stress was used to quantify monomer loss. Monomer peak area after shaking stress was reported as a percentage of the monomer peak area before stress exposure. These results are set forth in Table 14 below.

TABLE 14

| Formulation | PPG425 Conc. (mg/mL) | % monomer retained after shaking stress | |
|---|---|---|---|
| | | 23 hrs | 54 hrs |
| 7.1 | 0.5 | 98% | 98% |
| 7.2 | 1 | 99% | 99% |
| 7.3 | 2 | 100% | 99% |
| 7.4 | 5 | 99% | 98% |

Results from light absorbance, DLS particle size and size-exclusion HPLC (SE-HPLC) demonstrate the impact polypropylene glycol from 0.5 mg/mL to 5 mg/mL had in preventing aggregation of cetuximab after severe agitation and high exposure to air/liquid interface. Even in the presence of even low excipient concentration, formation of visible particles was prevented, as shown by absorbance data. Preservation of initial monomer size shown by DLS particle sizing data indicates suppression of soluble aggregate formation. SE-HPLC corroborates these measurements demonstrating essentially no loss of monomer in sample.

Example 8: Agitation Stress of Formulations Containing 10 mg/mL Cetuximab

This example compares the effect of the following additives in reducing particle formation in an agitated cetuximab formulation.

Materials:
Carboxymethylhydroxypropyl guar, CMHPG (Sigma-Aldrich, St. Louis)
Maltrin M100 (Grain Processing Corporation, Muscatine, Iowa)
Polyvinylpyrrolidone, 10 kDa (Sigma-Aldrich, St. Louis, Mo.)
Poly(2-ethyl-2-oxazoline), 5 kDa (Sigma-Aldrich, St. Louis, Mo.)
Poly(2-ethyl-2-oxazoline), 50 kDa (Sigma-Aldrich, St. Louis, Mo.)
Polypropylene glycol 1000 (Sigma-Aldrich, St. Louis, Mo.)
Pluronic F68 (BASF, Florham Park, N.J.)
Polysorbate 80 (Sigma-Aldrich, St. Louis, Mo.)

A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate. The Erbitux sample was reformulated in 10 mM sodium phosphate and 140 mM sodium chloride at pH 7 in the presence of about 100 ppm or about 200 ppm of stabilizing excipient in the following way. A stock buffer solution was prepared by dissolving 1.4 g sodium phosphate monobasic monohydrate (Sigma-Aldrich, St. Louis, Mo.), and about 8.2 g sodium chloride (Sigma-Aldrich, St. Louis, Mo.) in deionized water, and diluted to a final volume of 1 L with additional deionized water. The solution pH was adjusted to about 7 with the dropwise addition of 10 M sodium hydroxide. Stabilizing excipient was dissolved in the resulting buffer by adding 0.02 g or 0.04 g excipient to 50 mL of the stock buffer at pH 7. Excipient solutions were filtered through a 0.2 micron sterile polyethersulfone syringe filter (GE Healthcare Biosciences, Pittsburgh, Pa.), and 0.25 mL of each excipient solution added to a sterile 2 mL polypropylene tube along with stock buffer containing no excipient to achieve a volume of 0.71 mL prior to addition of concentrated cetuximab solution.

Amicon Ultra 15 centrifugal concentrator tubes with a 30 kDa nominal molecular weight cut-off (EMD-Millipore, Billerica, Mass.) were rinsed with deionized water, filled with 10 mL of Erbitux sample, and centrifuged in a Sorvall Legend RT centrifuge at about 3200×g and 23° C. to a final retentate volume of about 0.5 mL. The filtrate was then removed and about 0.29 mL was added to each sterile polypropylene tube, filtered through 0.2 micron sterile syringe filters.

The resulting cetuximab formulations in the 2 mL polypropylene tubes, having a concentration of about 10 mg/mL cetuximab and a final volume of about 1 mL, were placed on a Daigger Scientific (Vernon Hills, Ill.) Labgenius orbital shaker at 275 rpm. Samples were analyzed after 40 hours of continuous shaking by dynamic flow imaging with a FlowCam VS1 (Fluid Imaging Technologies, Scarborough, Me.).

The FlowCam was equipped with a 20× objective lens and a 50 micron depth flow cell, and operated at a flow rate of 0.03 mL/min. Measurements were made using a sample volume of 0.5 mL per run. Particles were counted and reported in four categories according to equivalent spherical diameter using the VisualSpreadsheet particle analysis software included with the instrument.

were prepared by dissolving 0.355 g sodium phosphate monobasic monohydrate (Sigma-Aldrich, St. Louis, Mo.), and about 2 g sodium chloride (Sigma-Aldrich, St. Louis, Mo.) in deionized water, and diluted to a final volume of 250 mL with additional deionized water. The solution pH was adjusted to about 7 with the dropwise addition of either 10 M sodium hydroxide. Stabilizing excipient was dissolved in the resulting buffer by adding 0.02 g excipient to 50 mL of the phosphate buffered saline at pH 7. Excipient solutions were filtered through 0.2 micron sterile polyethersulfone syringe filter (GE Healthcare Biosciences, Pittsburgh, Pa.), and either 1.0 mL or 0.5 mL of each excipient solution added to sterile 5 mL polypropylene tubes along with buffer containing no excipient to achieve a volume of about 3.8 mL prior to addition of concentrated cetuximab solution.

Amicon Ultra 15 centrifugal concentrator tubes with a 30 kDa nominal molecular weight cut-off (EMD-Millipore, Billerica, Mass.) were rinsed with deionized water, filled with 8.5 mL of Erbitux sample, and centrifuged in a Sorvall Legend RT centrifuge at about 3200×g and 23° C. to a final retentate volume of about 0.5 mL. The filtrate was then removed and about 0.21 mL was added to each sterile polypropylene tube, filtered through 0.2 micron sterile syringe filters.

TABLE 15

| Excipient ID | Excipient conc. (ppm) | FlowCam analysis (particles per mL) | | | | |
|---|---|---|---|---|---|---|
| | | 2-10 µm | 10-20 µm | 20-50 µm | >50 µm | Total |
| Polyvinylpyrrolidone, 10K | 100 | 564,764 | 126,021 | 5560 | 99 | 696,444 |
| Polysorbate 80 | 100 | 3160 | 172 | 49 | 0 | 3381 |
| Pluronic F68 | 100 | 357 | 12 | 0 | 0 | 369 |
| Poly(2-ethyl-2-oxazoline), 5K | 100 | 2230 | 320 | 0 | 0 | 2550 |
| Poly(2-ethyl-2-oxazoline), 50K | 200 | 46,040 | 14,826 | 6090 | 431 | 67,387 |
| PPG1000 | 100 | 1771 | 12 | 12 | 0 | 1795 |
| CMHPG | 100 | 1,418,745 | 659,587 | 308,738 | 14,509 | 2,401,579 |
| Maltrin M100 | 200 | 1,024,815 | 705,887 | 503,525 | 102,770 | 2,336,997 |
| None | 0 | 2,962,530 | 756,922 | 131,824 | 6697 | 3857973 |

Example 9: Polyvinyl Alcohol as Stabilizer Against Agitation Stress in Cetuximab Formulations This example compares the effect of the following additives in reducing particle formation in an agitated cetuximab formulation.

Materials:

Polyvinyl alcohol, 80% hydrolyzed, 9-10 kDa (Sigma-Aldrich, St. Louis, Mo.)

Polyvinyl alcohol, 87-89% hydrolyzed, 146-186 kDa (Sigma-Aldrich, St. Louis, Mo.)

Polypropylene glycol 1000 (Sigma Aldrich, St. Louis, Mo.)

A commercial cetuximab (ERBITUX®) drug product distributed in the U.S. by Eli Lilly & Co. was acquired. According to the FDA drug label, the commercial formulation contained 2 mg/mL cetuximab, 8.48 mg/mL sodium chloride, 1.88 mg/mL sodium phosphate dibasic heptahydrate and 0.41 mg/mL sodium phosphate monobasic monohydrate. The Erbitux sample was reformulated in 10 mM sodium phosphate and about 140 mM sodium chloride at pH 7 in the presence of about 50 ppm or about 100 ppm of stabilizing excipient in the following way. Buffer solutions The resulting cetuximab formulations in the 5 mL polypropylene tubes, having a concentration of about 2 mg/mL cetuximab and final volume of about 4 mL, were placed on a Daigger Scientific (Vernon Hills, Ill.) Labgenius orbital shaker at 275 rpm. After about 40 hours of continuous shaking, samples were pulled and analyzed by dynamic light scattering with a ZetaPlus from Brookhaven Instruments Corp. (Holtsville, N.Y.), and by dynamic flow imaging with a FlowCam VS1 (Fluid Imaging Technologies, Scarborough, Me.).

TABLE 16

| Excipient | | DLS effective particle size (nm) | |
|---|---|---|---|
| Identity | Conc. (ppm) | Initial | Final (after 40 hrs shaking) |
| Polyvinyl alcohol, 80% hydrolyzed | 100 | 11.4 | 11.4 |
| Polyvinyl alcohol, 80% hydrolyzed | 50 | 11.9 | 25,202 |
| Polyvinyl alcohol, 87-89% hydrolyzed | 100 | 11.9 | 12.0 |

TABLE 16-continued

| Excipient | | DLS effective particle size (nm) | |
|---|---|---|---|
| Identity | Conc. (ppm) | Initial | Final (after 40 hrs shaking) |
| Polyvinyl alcohol, 87-89% hydrolyzed | 50 | 13.2 | 14.4 |
| PPG1000 | 100 | 11.8 | 12.4 |
| None | 0 | 11.6 | 6817 |

The FlowCam was equipped with a 20× objective lens and a 50 micron depth flow cell, and operated at a flow rate of 0.03 mL/min. Measurements were made using a sample volume of 0.5 mL per run. Particles were counted and reported in four categories according to equivalent spherical diameter using the VisualSpreadsheet particle analysis software included with the instrument.

TABLE 17

| Excipient | | FlowCam analysis after 40 hrs shaking (particles/mL) | | | |
|---|---|---|---|---|---|
| Identity | Conc. (ppm) | 2-10 μm | 10-20 μm | 20-50 μm | >50 μm |
| Polyvinyl alcohol, 80% hydrolyzed | 100 | 1988 | 171 | 55 | 177 |
| Polyvinyl alcohol, 80% hydrolyzed | 50 | 153,069 | 22,153 | 10,960 | 1980 |
| Polyvinyl alcohol, 87-89% hydrolyzed | 100 | 335 | 61 | 6.1 | 0 |
| Polyvinyl alcohol, 87-89% hydrolyzed | 50 | 128,607 | 10,475 | 4130 | 775 |
| PPG1000 | 100 | 506 | 30 | 55 | 0 |
| None | 0 | 2,936,829 | 563,874 | 144,868 | 6800 |

In all cases the presence of the additive significantly reduced the number of particles generated during the agitation stress compared to sample with no additive, as demonstrated by the FlowCam data.

Example 10: The Impact of the Cellulosic Modification on the Stability of Cetuximab Formulations Two modified cellulosic materials, hydroxypropyl cellulose (HPC), and sodium carboxymethyl cellulose (CMC), were examined for their ability to stabilize cetuximab solutions to particle formation. The excipients were purchased from Sigma-Aldrich (St. Louis, Mo.) and used without further modification. Cetuximab was purchased under the trade name Erbitux® (Eli Lilly, Indianapolis, Ind.) from Clinigen Group (Yardley, Pa.). The HPC had a weight-average molecular weight of 80,000 and a number-average molecular weight of 10,000. The CMC had a weight-average molecular weight of 90,000. The number-average was not reported for the CMC. The cetuximab concentration was 2 mg/mL in all experiments. The HPC and CMC concentrations are listed in Table 18. A control sample with no stabilizing excipient was also prepared. All solutions were prepared in phosphate buffered saline, pH 7. Four mL of each sample was placed into sterile 5 mL polypropylene tubes. The samples were stressed by shaking on an orbital shaker at 275 rpm for 40 hours. Particulate formation was quantified by measuring the absorbance at 350 nm and the particle size was measured using dynamic light scattering (DLS). A Brookhaven ZetaPlus instrument was used to perform the DLS experiments. The cumulants expansion was fit the DLS intensity autocorrelation functions to estimate the particle sizes. DLS measurements were made both prior to and after shaking.

Solutions containing HPC are less turbid than the control (Table 18) and the apparent particle size does not change during the experiment, indicating that HPC is effective in stabilizing cetuximab towards particle formation. However, solutions containing CMC have turbidities and final particle sizes similar to that of the control, indicating that CMC is not effective in stabilizing cetuximab towards particle formation. The results here illustrate that the type of modification is important in the ability of the cellulosic material to protect against particulate formation in protein solutions.

TABLE 18

| Sample | Cellulosic concentration (ppm) | Absorbance at 350 nm (AU) | Initial DLS particle size (nm) | Final DLS particle size (nm) |
|---|---|---|---|---|
| Control | N/A | 0.749 | 12.2 | 10,421 |
| CMC | 2151 | 0.560 | 14.1 | 13,936 |
| CMC | 203 | 0.628 | 11.9 | 17,620 |
| HPC | 1850 | 0.071 | 14.0 | 13.3 |
| HPC | 199 | 0.065 | 11.9 | 11.8 |

Example 11: Excipients that Stabilize Cetuximab Formulations to Particle Formation In this example, cetuximab at 2 mg/mL is stressed in the presence of several different stabilizing excipients. The excipients are polyvinyl pyrrolidone (PVP) with weight-average molecular weight of 40,000, polyvinyl alcohol (PVOH) with weight-average molecular weight of 13,000-23,000 and 87-89% hydrolyzed residues, 2-hydroxyethyl cellulose (HEC) with viscosity-average molecular weight of 90,000, and poly(2-ethyl-2-oxazoline) (PDX5000) with number-average molecular weight of 5000 and polydispersity less than or equal to 1.2, and aspartame. The excipients were purchased from Sigma-Aldrich (St. Louis, Mo.) and used without further modification. Cetuximab was purchased under the trade name ERBITUX® (Eli Lilly, Indianapolis, Ind.) from Clinigen Group (Yardley, Pa.). The concentrations of each excipient are listed in Table 19. A control sample was also prepared with no stabilizing excipient. All experiments were performed in a phosphate buffered saline at pH 7. Four mL of each sample was put into sterile 5 mL polypropylene tubes, which were then placed on an orbital shaker set to 275 rpm. The samples were shaken for 40 hours, after which they were analyzed for particulate formation by an absorbance measurement at 405 nm to estimate turbidity and the total number of particles were counted using a FlowCam imaging device. The turbidity measurements were performed with a BioTek Synergy plate reader and corrected for the path length of the liquid height in the microplate. The FlowCam was equipped with a 20× objective lens and a 50 μm depth flow cell, and operated at a flow rate of 0.03 mL/min. Measurements were made using a sample volume of 0.5 mL per run. The control sample was run through the FlowCam last and partially clogged the flow cell, which prevented an accurate particle count. This makes the number listed in Table 19 a lower bound on the total number of particles. At the use levels indicated in Table 19, all of the additives stabilize cetuximab to particulate formation as indicated by a reduction in the absorbance at 405 nm and a reduction in the total number of particles per mL.

TABLE 19

| Sample | Excipient concentration (ppm) | Absorbance at 405 nm (AU) | % Reduction of ABS405 nm | Number of particles per mL | % Reduction in particles per mL |
|---|---|---|---|---|---|
| Control | N/A | 0.340 | 0 | >1,184,884 | 0 |
| PVP | 1801 | 0.044 | 87 | 14,868 | >98.7 |
| PVOH | 197 | 0.032 | 90 | 898 | >99.9 |
| HEC | 199 | 0.041 | 88 | 7559 | >99.4 |
| POX5000 | 197 | 0.040 | 88 | 15,112 | >98.7 |
| Aspartame | 5886 | 0.066 | 81 | 423,636 | >64.2 |

Example 12: The Foaming Propensity of Stabilizing Excipients

Solutions of concentration 1000 ppm w/v of poly(propylene glycol) with $M_n$ 1000 (PPG1000, Sigma Aldrich, St. Louis, Mo.), poly(2-ethyl-2-oxazoline) with $M_n$ 5000 and PDI≤1.2 (POX5000, Sigma Aldrich, St. Louis, Mo.), Methocel E3LV (Dow Chemical Company, Midland, Mich.), polysorbate 80 (PS80, Sigma Aldrich, St. Louis, Mo.), and Pluronic F68 (F68, BASF Corporation) were prepared using ultrapure deionized water (18.2 MΩ·cm at 25° C.). 3 mL of each solution was placed into a 5-mL polypropylene tube and vortexed on a Mini Vortex Mixer (VWR, Radnor, Pa.) on mixer setting #8 for 15 seconds. The foam heights were measured after vortexing and are listed in Table 20. The times for the foams to dissipate were also recorded and are listed in Table 20. The foams for the POX5000 and F68 samples did not dissipate over the course of the experiment. The stopping points are listed in Table 20.

TABLE 20

| Excipient | Foam height (in) | Foam dissipation time (s) |
|---|---|---|
| PPG1000 | 0.25 | 4 |
| POX5000 | 0.63 | 27 |
| Methocel E3LV | 1.00 | >1125 |
| PS80 | 0.25 | 7 |
| F68 | 1.25 | >1125 |

Example 13: The Recovery of Stabilizing Excipients after Ultrafiltration

Solutions of concentration 1000 ppm w/v of poly(propylene glycol) with $M_n$ 1000 (PPG1000, Sigma Aldrich, St. Louis, Mo.), poly(2-ethyl-2-oxazoline) with $M_n$ 5000 and PDI≤1.2 (POX5000, Sigma Aldrich, St. Louis, Mo.), Methocel E3LV (Dow Chemical Company, Midland, Mich.), polysorbate 80 (PS80, Sigma Aldrich, St. Louis, Mo.), and Pluronic F68 (F68, BASF Corporation) were prepared using ultrapure deionized water (18.2 MΩ·cm at 25° C.).

The filter devices used are Amicon Ultra-4 centrifugal devices with 30,000 molecular weight cut-off (EMD Millipore). A Sorvall Legend RT Centrifuge was used to filter the feed volume through the membrane at 4,000 rpm for 10 minutes at 25° C. An Agilent 1100 HPLC system with attached refractive index detector (RID) was used to measure the concentration of the material in feed, retentate and filtrate volumes.

A standard curve was prepared initially for each solution. Concentrations of 1000, 700, 500, 400, 200 and 100 ppm were prepared and analyzed on HPLC-RID to determine peak area. The peak area was then plotted against concentration and a linear response was observed for all solutions at a range from 100-1000 ppm.

The filter devices were pre-rinsed by addition of 4 mL of DI water and centrifugation for 10 minutes at 4,000 rpm and 25° C. The filtered rinse water was then discarded before the addition of 4 mL of 1000 ppm excipient solution. The samples were then centrifuged using conditions as stated above. The filtrate from filter devices was emptied into clean 30 mL tubes (tare weighed) after centrifugation. The process was repeated four additional times for a total of 20 mL filtrate material. The total amount of filtrate was determined by mass. Each condition was performed in triplicate.

A volume of 100 μL of stock, retentate, and filtrate was removed and 20 μL injections were prepared to determine peak area by refractive index detection (RID). Using the standard curve formula, the concentrations were determined by inputting the peak areas. The amount of excipient recovered in the filtrate and retentate was determined by multiplying the total filtrate and retentate volumes by the measured concentrations. The mass of excipient recovered in the filtrate was compared to the initial mass added to filtration device to determine a percent recovery.

The percent recoveries of the excipients studied here are given in Table 21. The recoveries of PPG1000, Methocel E3LV, POX5000, and Pluronic F68 are greater than those of PS80.

TABLE 21

| Excipient | Mass excipient added (mg) | Mass excipient in retentate (mg) | Mass excipient recovered in filtrate (mg) | Percent recovered in filtrate | Average percentage recovered in filtrate |
|---|---|---|---|---|---|
| PS80 | 20.1 | 10.4 | 8.72 | 43.4% | 40.5% |
|  | 20.1 | 10.2 | 7.84 | 39.0% |  |
|  | 20.1 | 10.0 | 7.87 | 39.1% |  |
| PPG1000 | 20.2 | 0.35 | 20.7 | 102% | 103% |
|  | 20.2 | 0.35 | 20.6 | 102% |  |
|  | 20.2 | 0.35 | 21.2 | 105% |  |
| POX5000 | 20.2 | 0.45 | 19.9 | 98.4% | 100% |
|  | 20.2 | 0.45 | 20.4 | 101% |  |
|  | 20.2 | 0.44 | 20.3 | 101% |  |
| Methocel E3LV | 16.7 | 4.71 | 13.8 | 82.6% | 79.6% |
|  | 16.7 | 4.12 | 12.9 | 77.4% |  |
|  | 16.7 | 4.86 | 13.1 | 78.9% |  |
| F68 | 23.8 | 0.81 | 21.55 | 90.6% | 90.7% |
|  | 23.8 | 0.81 | 21.62 | 90.8% |  |
|  | 23.8 | 0.84 | 21.58 | 90.7% |  |

Example 14: Excipients that Stabilize Abatacept

Abatacept was purchased under the trade name ORENCIA® (Bristol-Meyers Squibb, Princeton, N.J.) from the Clinigen Group (Yardley, Pa.). Orencia was reconstituted to 25 mg/mL abatacept in ultrapure deionized water with resistivity of 18.2 MΩ·cm (EMD Millipore, Billerica, Mass.) as per the package insert instructions. A 14-mM monosodium phosphate buffer (Sigma Aldrich, St. Louis, Mo.), pH 7.5 with 25 mM NaCl (Sigma Aldrich, St. Louis, Mo.) was prepared. Stock solutions of concentration 2000 ppm by weight of poly(propylene glycol) with $M_n$ 1000 (PPG1000, Sigma Aldrich, St. Louis, Mo.), poly(2-ethyl-2-oxazoline) with $M_n$ 5000 and PDI≤1.2 (PDX5000, Sigma Aldrich, St. Louis, Mo.), and Methocel E3LV (Dow Chemical Company, Midland, Mich.) were prepared using the previously described buffer. Samples were prepared by mixing the reconstituted Orencia with the excipient stock solution and the buffer to a final protein concentration of 2.5 mg/mL, final excipient concentrations of approximately 1800 ppm and 200 ppm. 1 mL of each sample was placed into a sterile 2 mL polypropylene tube. The tubes were shaken for 18 hours at 25° C. on a Multi-Therm Shaker (Southwest Science, Roebling, N.J.). An unstressed control sample with no excipient was also included (Sample 1, Table 22). The samples were assayed for apparent particle size by dynamic light scattering (DLS) and total particle count by FlowCam imaging. Forty µL of each sample was loaded into a 384-well microplate (Aurora Microplates, Whitefish, Mont.). Air bubbles were removed from the microplate by centrifuging the plate at 400×g for 1 minute. The plate was then assayed for apparent particle size by DLS (DynaPro Plate Reader II, Wyatt, Santa Barbara, Calif.). The instrument control and data fitting were performed using the DYNAMICS software package (Wyatt, Santa Barbara, Calif.). The incident wavelength was 830 nm and the scattering angle was 158°. The intensity autocorrelation functions were generated using five 5-second exposures and were fit to the cumulants expansion to estimate the particle diffusivity. The apparent hydrodynamic radii (Rh) were calculated from the diffusivities via the Stokes-Einstein relation. Sub-visible particle (greater than 2 microns in size) formation was quantified using a FlowCam VS1 analyzer (Fluid Imaging Technologies, Scarborough, Me.). The FlowCam was equipped with a 20× objective lens and a 50-micron depth flow cell, and operated at a flow rate of 0.03 mL/min. 0.5 mL of each sample was assayed for particle counts.

All of the excipients in this example stabilize abatacept formulations to a shaking stress as indicated by a decrease in the particle count and hydrodynamic size as compared to the control (Sample 2, Table 22).

TABLE 22

| Sample | Excipient | Excipient concentration (ppm) | Stressed? (Yes/No) | $R_h$ (nm) | Particles/ mL |
|---|---|---|---|---|---|
| 1 | None | N/A | No | 5.3 | 571 |
| 2 | None | N/A | Yes | 65.6 | 292,413 |
| 3 | PPG1000 | 1800 | Yes | 5.0 | 3591 |
| 4 | POX5000 | 1750 | Yes | 7.8 | 1021 |
| 5 | Methocel E3LV | 2020 | Yes | 5.3 | 2595 |
| 6 | PPG1000 | 200 | Yes | 5.1 | 4550 |
| 7 | POX5000 | 195 | Yes | 6.2 | 69,474 |
| 8 | Methocel E3LV | 225 | Yes | 5.1 | 2813 |

Example 15: PPG1000 Ultrafiltration without Concentration

Poly(propylene glycol) 1000 (PPG1000), purchased from Sigma-Aldrich, was prepared at a concentration of 1000 ppm (0.1%) in ultrapure deionized (DI) water (18.2 MΩ·cm). Polysorbate 80 (PS80), purchased from Sigma-Aldrich, was prepared at a concentration of 1000 ppm (0.1%) in ultrapure deionized (DI) water (18.2 MΩ·cm). The PPG1000 and PS80 solutions were processed by ultrafiltration in the following way. Amicon Ultra-4 centrifugal filter devices with a 30,000 molecular weight cut-off (EMD Millipore) were pre-rinsed with 5 mL of DI water. A Sorvall Legend RT Centrifuge was used to spin down the DI water to wash filter membrane at 4000 rpm for 10 minutes at 24° C. A total of 3 washes were completed for a total wash volume of 15 mL of DI water before samples were placed in the filter devices. After rinsing the filter devices, 5 mL of PPG1000 or PS80 at 0.1% was added and the devices were centrifuged at 4000 rpm for 5 minutes at 24° C. A volume of 100 µL of retentate and filtrate were removed from the filtration devices for analysis using a refractive index detector (RID) in line with an Agilent 1100 HPLC system.

The relative concentrations of PPG1000 and PS80 in the starting solution, the retentate, and the filtrate were measured with the HPLC/RID system. The retentate and filtrate peak areas listed in Table 23 for PPG1000 are nearly identical, indicating that PPG1000 does not concentrate in the retentate during ultrafiltration. In the same ultrafiltration conditions, PS80 concentrates in the retentate by a factor of 90 compared to the initial stock concentration and is depleted in the filtrate by a factor of 20 less than the initial stock concentration as shown by the peak areas recorded in Table 23.

TABLE 23

| Test No. | Stock solution | Stock Solution (peak area) | Retentate (peak area) | Filtrate (peak area) |
|---|---|---|---|---|
| 1 | 0.1% PS80 | 40,794 | 3,617,387 | 2,109 |
| 2 | 0.1% PS80 | 40,794 | 3,623,979 | 2,330 |
| 3 | 0.1% PS80 | 40,794 | 2,940,782 | [no detectable PS80] |
| 4 | 0.1% PPG1000 | 162,226 | 166,405 | 165,743 |
| 5 | 0.1% PPG1000 | 162,226 | 164,225 | 165,307 |
| 6 | 0.1% PPG1000 | 162,226 | 163,976 | 167,556 |

EQUIVALENTS

While specific embodiments of the subject invention have been disclosed herein, the above specification is illustrative and not restrictive. While this invention has been particularly shown and described with references to preferred embodiments thereof, it will be understood by those skilled in the art that various changes in form and details may be made therein without departing from the scope of the invention encompassed by the appended claims. Many variations of the invention will become apparent to those of skilled art upon review of this specification. Unless otherwise indicated, all numbers expressing reaction conditions, quantities of ingredients, and so forth, as used in this specification and the claims are to be understood as being modified in all instances by the term "about." Accordingly, unless indicated to the contrary, the numerical parameters set forth herein are approximations that can vary depending upon the desired properties sought to be obtained by the present invention.

What is claimed is:

1. A therapeutic formulation comprising an antibody and a stabilizing amount of a polypropylene glycol homopolymer, wherein the antibody is in an amount of at least about 2 mg/mL, wherein the polypropylene glycol homopolymer has a number-average molecular weight between about 300 and about 5000, and wherein the stabilizing amount of the polypropylene glycol homopolymer is between about 10 and about 1000 ppm.

2. The therapeutic formulation of claim 1, wherein the formulation is suitable for injection.

3. The therapeutic formulation of claim 2, wherein the formulation further comprises an aqueous medium.

4. The therapeutic formulation of claim 1, wherein the formulation contains at least about 5 mg/mL of the antibody.

5. The therapeutic formulation of claim 4, wherein the formulation contains at least about 100 mg/mL of the antibody.

6. The therapeutic formulation of claim 1, wherein the formulation contains between about 10 and about 500 ppm of the polypropylene glycol homopolymer.

7. The therapeutic formulation of claim 6, wherein the formulation contains between about 10 and about 100 ppm of the polypropylene glycol homopolymer.

8. The therapeutic formulation of claim 1, wherein the polypropylene glycol homopolymer has a number-average molecular weight of about 425 Daltons.

9. The therapeutic formulation of claim 1, wherein the polypropylene glycol homopolymer is a linear polymer comprising at least two hydroxyl groups.

10. The therapeutic formulation of claim 1, wherein the formulation does not contain an additional surfactant.

11. The formulation of claim 1, further comprising a buffer.

12. The therapeutic formulation of claim 1, wherein the polypropylene glycol homopolymer is added in an amount effective to reduce degradation of the formulation by at least 50%, as compared to a control formulation, wherein the control formulation is identical on a dry weight basis to the therapeutic formulation except that it lacks the polypropylene glycol homopolymer.

13. The therapeutic formulation of claim 12, wherein the polypropylene glycol homopolymer is added in an amount effective to reduce degradation of the formulation by at least 70%, as compared to the control formulation.

14. The therapeutic formulation of claim 13, wherein the polypropylene glycol homopolymer is added in an amount effective to reduce degradation of the formulation by at least 90%, as compared to the control formulation.

15. The therapeutic formulation of claim 1, wherein the polypropylene glycol homopolymer is added in an amount effective to reduce aggregation or precipitation of the antibody during a cold storage condition.

16. The therapeutic formulation of claim 1, wherein the polypropylene glycol homopolymer is added in an amount effective to reduce aggregation or precipitation of the antibody during an elevated storage condition.

17. The therapeutic formulation of claim 1, wherein the therapeutic formulation is resistant to foaming.

18. The therapeutic formulation of claim 1, wherein the therapeutic formulation is resistant to micelle formation.

19. The therapeutic formulation of claim 1, wherein the therapeutic formulation has improved stability as compared to a control formulation, when the therapeutic formulation is exposed to a stress condition, and wherein the control formulation is identical on a dry weight basis to the therapeutic formulation except that it lacks the polypropylene glycol homopolymer.

20. The therapeutic formulation of claim 19, wherein the stress condition is selected from the group consisting of agitation stress, exposure to air/water interfaces, contact with plastic, glass, or metal surfaces, filtration, column chromatography separation, viral inactivation, exposure to pH conditions between pH 2 and pH 5, exposure to pH conditions between pH 8 and pH 12, exposure to proteolytic enzymes, exposure to lipase enzymes, and exposure to microbiological contamination.

21. The therapeutic formulation of claim 19, wherein the stress condition is selected from the group consisting of oxidation, hydrolysis, proteolysis, deamidation, disulfide scrambling, photodegradation, and microbial degradation.

22. A method of improving stability in a therapeutic formulation comprising an antibody, wherein the method comprises adding a stability-improving amount of a polypropylene glycol homopolymer to the therapeutic formulation, wherein the antibody is in an amount of at least about 2 mg/mL, wherein the polypropylene glycol polymer has a number-average molecular weight between about 300 and about 5000, and wherein the stabilizing amount of the polypropylene glycol homopolymer is between about 10 and about 1000 ppm.

23. The method of claim 22, wherein the polypropylene glycol homopolymer has a number-average molecular weight of about 425 Daltons.

24. The method of claim 22, wherein the polypropylene glycol homopolymer reduces degradation of the therapeutic formulation by at least 50%, as compared to a control formulation, wherein the control formulation is identical on a dry weight basis to the therapeutic formulation except that it lacks the polypropylene glycol homopolymer.

25. The method of claim 24, wherein the polypropylene glycol homopolymer reduces degradation of the therapeutic formulation by at least 70%, as compared to the control formulation.

26. The method of claim 25, wherein the polypropylene glycol homopolymer reduces degradation of the therapeutic formulation by at least 90%, as compared to the control formulation.

* * * * *